(12) United States Patent
Chang et al.

(10) Patent No.: US 11,833,289 B2
(45) Date of Patent: Dec. 5, 2023

(54) POLYMER AND DEVICE FOR CAPTURING OR SEPARATING LEUCOCYTES, MANUFACTURING METHOD AND USE THEREOF

(71) Applicant: Puriblood Medical Co., Ltd., Hsinchu County (TW)

(72) Inventors: Yung Chang, Taoyuan (TW); Chih-Chen Yeh, Taipei (TW); Cheng-Chen Yang, Taoyuan (TW); Jheng-Fong Jhong, Hsinchu (TW)

(73) Assignee: PURIBLOOD MEDICAL CO., LTD., Hsinchu County (TW)

( * ) Notice: Subject to any disclaimer, the term of this patent is extended or adjusted under 35 U.S.C. 154(b) by 981 days.

(21) Appl. No.: 16/348,325

(22) PCT Filed: Nov. 9, 2017

(86) PCT No.: PCT/CN2017/110177
§ 371 (c)(1),
(2) Date: Jul. 24, 2019

(87) PCT Pub. No.: WO2018/086556
PCT Pub. Date: May 17, 2018

(65) Prior Publication Data
US 2019/0359752 A1    Nov. 28, 2019

Related U.S. Application Data

(60) Provisional application No. 62/419,600, filed on Nov. 9, 2016.

(51) Int. Cl.
*A61M 1/36* (2006.01)
*A61M 1/02* (2006.01)
(Continued)

(52) U.S. Cl.
CPC ........ *A61M 1/3679* (2013.01); *A61M 1/0281* (2013.01); *A61M 1/3496* (2013.01);
(Continued)

(58) Field of Classification Search
CPC .............. A61M 1/0281; A61M 1/3496; A61M 1/3633; A61M 1/3679; A61M 2202/0439;
(Continued)

(56) References Cited

U.S. PATENT DOCUMENTS

| 5,407,581 A | 4/1995 | Onodera et al. |
| 2012/0024779 A1* | 2/2012 | Ochiai ................... B01D 29/00 524/558 |

FOREIGN PATENT DOCUMENTS

| CN | 101358015 A | 2/2009 |
| CN | 102292115 A | 12/2011 |

(Continued)

OTHER PUBLICATIONS

Kazuo Sugiyama et al., Chemistry Letters, vol. 26, No. 3, Mar. 1, 1997, pp. 219-220.*
(Continued)

*Primary Examiner* — John Kim
(74) *Attorney, Agent, or Firm* — Lippes Mathias LLP

(57) ABSTRACT

Disclosed is a polymer for capturing or separating leukocytes. The polymer is prepared by a polymerization reaction
(Continued)

of monomers containing an amino and a hydroxyl. The monomer containing an amino and a hydroxyl has the structure of formula (1):

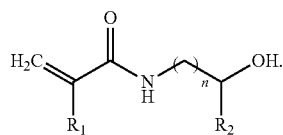

(1)

In formula (1), R1 is independently selected from the group consisting of a hydrogen, a methyl, an ethyl, a hydroxyl, any one of C1 to C12 long carbon chains, and a benzene ring, R2 is independently selected from the group consisting of a hydrogen, a methyl, an ethyl, any one of from C1 to C6 long carbon chains, an amino and a benzene ring, and n is an integer of 1 to 5.

11 Claims, 15 Drawing Sheets

(51) Int. Cl.
*A61M 1/34* (2006.01)
*B01D 39/16* (2006.01)
*C08F 220/56* (2006.01)
*C08F 220/58* (2006.01)
*C08F 222/38* (2006.01)
*C08J 7/16* (2006.01)
*B01D 39/06* (2006.01)

(52) U.S. Cl.
CPC ............ *A61M 1/3633* (2013.01); *B01D 39/06* (2013.01); *C08F 220/56* (2013.01); *C08F 220/58* (2013.01); *C08F 222/385* (2013.01); *C08J 7/16* (2013.01); *A61M 2202/0439* (2013.01); *B01D 2239/0407* (2013.01); *B01D 2239/0478* (2013.01); *C08J 2333/26* (2013.01)

(58) Field of Classification Search
CPC ............ B01D 39/16; B01D 2239/0407; B01D 2239/0478; C08F 220/56; C08F 220/58; C08F 222/385; C08J 7/16; C08J 2333/26
See application file for complete search history.

(56) References Cited

FOREIGN PATENT DOCUMENTS

| CN | 105813663 A | 7/2016 |
|---|---|---|
| CN | 105985482 A | 10/2016 |
| JP | S 6168454 A | 4/1986 |

OTHER PUBLICATIONS

Chao Zhao et al., Biomaterials, vol. 34, No. 20, Apr. 2, 2013, pp. 4714-4724.*
Toshinori Morisaku et al., "Hydration of phosphorylcholine groups attached to highly swollen polymer hydrogels studied by thermal analysis," Polymer 49, Aug. 19, 2008, pp. 4652-4657.
Shenfu Chen et al., "Surface hydration: Principles and applications toward low-fouling/nonfouling biomaterials," Polymer 51, Aug. 18, 2010, pp. 5283-5293.
Higuchi, A. et al., "D.s.c. investigation of the states of water in poly(vinyl alcohol-co-itaconic acid) membranes", Polymer 26, 1985, pp. 1833-1837.
Higuchi, A. et al., "D.s.c. investigation of the states of water in poly(vinyl alcohol-co-itaconic acid) membranes", Polymer 26, 1984, pp. 1207-1211.
Tanaka, M. et al., "Effect of water structure on blood compatibility-thermal analysis of water in poly (meth) acrylate", Journal of Biomedical Materials Research Part A, 2004.68(4), p. 684-695.
Tsai, W.B. et al., "Platelet adhesion to polystyrene-based surfaces preadsorbed with plasmas selectively depleted in fibrinogen, fibronectin, vitronectin, or von Willebrand's factor", Journal of biomedical materials research, 2002, 60(3), p. 348-359.
Carl G Gahmberg, "Leukocyte adhesion: CD11/CD18 integrins and intercellular adhesion molecules", Current Opinion in Cell Biology, 1997, 9, p. 643-650.
International Search Report dated Feb. 8, 2018 from PCT/CN2017/110177.

* cited by examiner

POLYMER AND DEVICE FOR CAPTURING OR SEPARATING LEUCOCYTES, MANUFACTURING METHOD AND USE THEREOF

This is a 371 of PCT Patent Application Ser. No. PCT/CN2017/110177 filed Nov. 9, 2017, which claims priority to U.S. Provisional Patent Application Ser. No. 62/419,600 filed Nov. 9, 2016.

BACKGROUND

Field of Invention

Examples of the present invention relate to a material for capturing or separating cells, and more particularly to a polymer for capturing or separating leukocytes.

Description of Related Art

Blood transfusion supplements the blood composition lacking in a patient by infusion of blood product from donors into the patient's body. Blood product (or called as blood component) mainly includes whole blood, plasma, washed erythrocyte, erythrocyte concentrate, leukocyte concentrate, and platelet concentrate. During blood transfusion, the blood component to be input can be selected according to a patient's needs.

It is known that many adverse responses after blood transfusion are associated with leukocytes or the cytokines released from leukocytes. The adverse responses include, for example, non-hemolytic febrile transfusion reactions (NHFTR), alloimmunization, transfusion-associated graft versus host disease (TA-GVHD), or the like. Therefore, in many countries, leukocyte depletion has been regulated as a necessary procedure for blood transfusion regardless of erythrocyte or platelet transfusion, and the concentration of leukocyte in the blood should reduce to below a certain level in order to prevent the above-mentioned adverse responses.

The conventional leukocyte separation is performed by using filter material having electrically charged surface. However, separating leukocytes via an electrically charged surface is prone to increase the concentration of bradykinin, which is prone to induce hypotensive transfusion reaction during blood transfusion.

In addition, in order to avoid blood coagulation or activation of platelets during blood transfusion or blood treatment, an anticoagulant is generally added to the blood sample, or surface treatment is conducted on the surface of the filter material to prevent blood coagulation or activation of platelets. At present, in the technical field of leukocyte depletion, there is not yet a suitable filter material which can effectively solve the above-mentioned problems of the prior art.

SUMMARY

An object of the present invention is to provide a material having the ability to capture or separate leukocytes; preferably, the material has the ability to avoid fibrinogen adsorption and/or platelet attachment; thus a high level of platelet retention rate during leukocyte depletion process is achieved.

One aspect of the invention is a polymer which is a material for capturing or separating leukocytes. The polymer is prepared by a polymerization reaction using an amide-hydroxyl-containing monomer, wherein the amide-hydroxyl-containing monomer has the structure of the formula (1):

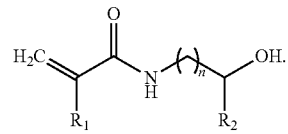

(1)

In formula (I), $R_1$ is independently selected from the group consisting of hydrogen, methyl, ethyl, hydroxyl, one of from C1 to C12 carbon chain, and benzene ring; $R_2$ is independently selected from the group consisting of hydrogen, methyl, ethyl, one of from C1 to C6 carbon chain, amine group, and benzene ring; and n is an integer of 1 to 5.

According to some embodiments of the invention, in formula (1), $R_1$ is hydrogen, $R_2$ is hydrogen, and n is 1.

According to some embodiments of the present invention, the amide-hydroxyl-containing monomer is N-hydroxyethyl acrylamide or N-(2-hydroxyethyl) acrylamide.

According to some embodiments of the invention, the polymer is a copolymer copolymerized from the amide-hydroxyl-containing monomer and at least one other monomer.

According to some embodiments of the invention, the at least one other monomer is butyl methacrylate (BMA) or glycidyl methacrylate (GMA).

According to some embodiments of the invention, the polymer is a segmented polymer.

According to some embodiments of the invention, the polymer is a crosslinked polymer.

According to some embodiments of the invention, the polymerization reaction comprises using a crosslinking agent, and the crosslinking agent has a diacrylate functional group.

According to some embodiments of the invention, the crosslinking agent is N,N'-methylenebisacrylamide (NMBA), ethylene glycol dimethacrylate (EGDMA), PLA-PEG-PLGA copolymer, or poly(ethylene glycol) diacrylate (PEGDA).

One aspect of the invention is a device for capturing or separating leukocytes; the device comprises a housing and a body. The body comprises a polymer, and the polymer comprises the structure of formula (2):

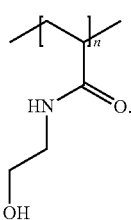

(2)

In formula (2), n is an integer of 10 to 50.

According to some embodiments of the invention, the polymer has the structure of formula (3):

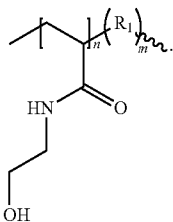
(3)

In formula (3), m is an integer of 50 to 90, and

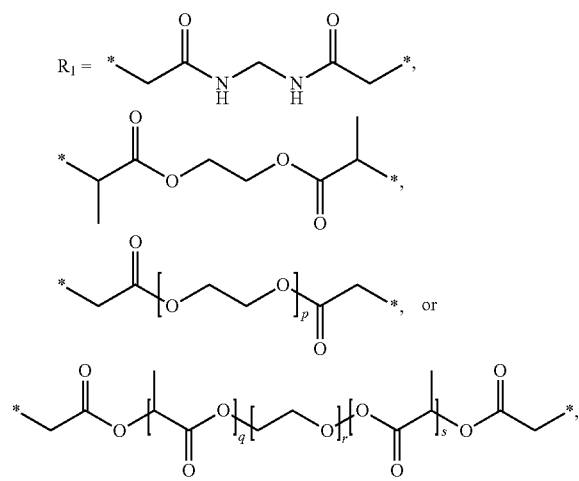

wherein p is an integer of 2 to 6, q is an integer of 1 to 6, r is an integer of 1 to 6, and s is an integer of 1 to 6.

According to some embodiments of the invention, the polymer has the structure of formula (4):

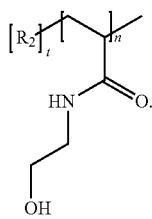
(4)

In formula (4), t is an integer of 50 to 90, and

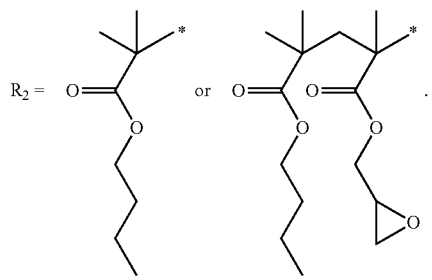

According to some embodiments of the invention, the body comprises a substrate, wherein the polymer is disposed on the substrate in manners such as coating, spraying, or impregnating.

According to some embodiments of the invention, the body comprises a substrate, wherein the polymer is anchored to the substrate in an anchoring manner.

According to some embodiments of the invention, the elements of the surface of the filter material comprise carbon, oxygen, and nitrogen; the total mole percentage of carbon, oxygen, and nitrogen is defined as 100 mole %, the mole percentage of carbon is from about 76.22% to about 79.84%, the mole percentage of oxygen is from about 18.1% to about 21.04%, and the mole percentage of nitrogen is from about 2.05% to about 2.75%.

One aspect of the invention is the use of an amide-hydroxyl-containing polymer for capturing or separating leukocytes. The amide-hydroxyl-containing polymer comprises the structure of formula (2):

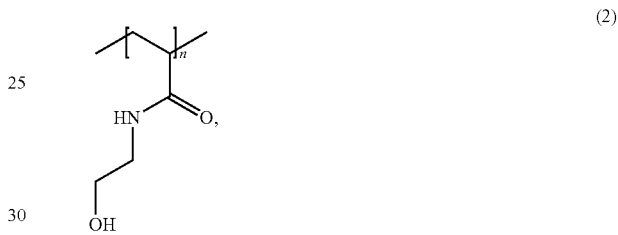
(2)

wherein n is an integer of 10 to 50.

According to some embodiments of the invention, the leukocyte capture rate of the amide-hydroxyl-containing polymer is not less than 70%.

According to some embodiments of the invention, the platelet retention rate for the amide-hydroxyl-containing polymer is not less than 85%.

One aspect of the invention is the use of an amide-hydroxyl-containing monomer for manufacturing a filter material for capturing or separating leukocytes. The amide-hydroxyl-containing monomer has the structure of formula (I):

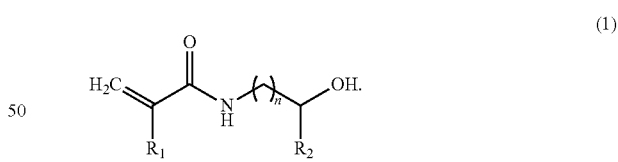
(1)

In formula (I), $R_1$ is independently selected from the group consisting of hydrogen, methyl, ethyl, one of from C1 to C12 carbon chain, and benzene ring; $R_2$ is independently selected from the group consisting of hydrogen, methyl, ethyl, one of from C1 to C6 carbon chain, amino group, and benzene ring; and n is an integer of 1 to 5.

According to some embodiments of the invention, wherein the step of manufacturing a filter material for capturing or separating leukocytes comprises providing a substrate and modifying the substrate with the amide-hydroxyl-containing monomer.

According to some embodiments of the invention, modifying the substrate with the amide-hydroxyl-containing monomer comprises: providing amide-hydroxyl-containing monomer; providing at least one anchoring unit; polymerizing the amide-hydroxyl-containing monomer with the anchoring unit to form a copolymer; and anchoring the copolymer on the substrate via the anchoring unit.

According to some embodiments of the invention, the amide-hydroxyl-containing monomer accounts for about 20 to about 40 weight percent of the copolymer.

According to some embodiments of the invention, the anchoring unit accounts for about 60 to about 80 weight percent of the copolymer.

According to some embodiments of the invention, the anchoring unit is selected from the group consisting of butyl methacrylate, glycidyl methacrylate, and a combination thereof.

According to some embodiments of the invention, wherein the step of modifying the substrate with the amide-hydroxyl-containing monomer includes coating the amide-hydroxyl-containing monomers on the substrate, and treating the amide-hydroxyl-containing monomers with ultraviolet (UV) rays.

One aspect of the present invention provides a method for preparing a leukocyte concentrate; the method comprises: providing the above-mentioned device for capturing or separating leukocytes; providing a blood sample, wherein the blood sample comprises leukocytes and platelets; passing the blood sample through the device, so that the leukocytes are captured in the device or separated from the blood sample; and desorbing of the captured or separated leukocytes.

One aspect of the present invention provides a method for preparing an erythrocyte concentrate; the method comprises: providing the above-mentioned device for capturing or separating leukocytes; providing a blood sample, wherein the blood sample comprises erythrocytes, leukocytes, and platelets; passing the blood sample through the device and acquiring a filtrate, wherein the leukocytes are captured in the device or separated from the blood sample; and treating the filtrate to form an erythrocyte concentrate.

One aspect of the present invention provides a method for treating a plasma product prior to storage; the method comprises: providing the above-mentioned device for capturing or separating leukocytes; providing a blood sample, wherein the blood sample comprises leukocytes and platelets; and passing the blood sample through the device and acquiring a filtrate, wherein the leukocytes are captured in the device or separated from the blood sample.

One aspect of the present invention provides a method for removing leukocytes from whole blood; the method comprises: providing the above-mentioned device for capturing or separating leukocytes; providing a whole blood sample, wherein the whole blood sample comprises erythrocytes, leukocytes, and platelets; and passing the whole blood sample through the device and acquiring a filtrate, wherein the leukocytes are captured in the device or separated from the whole blood sample.

A method for preparing a platelet concentrate comprises: providing the above-mentioned device for capturing or separating leukocytes; providing a blood sample, wherein the blood sample comprises leukocytes and platelets; passing the blood sample through the device and acquiring a filtrate, wherein the leukocytes are captured in the device or separated from the blood sample; and treating the filtrate to form a platelet concentrate. Wherein the blood sample may be a whole blood sample or an erythrocyte reduced blood sample treated with centrifugation.

In summary, the present invention provides a polymer or a device for capturing or separating leukocytes, a manufacturing method, and a use thereof. An amide-hydroxyl-containing compound or a polymer formed by using the compound as a monomer provides functions for capturing or separating leukocytes. Since such compound and polymer have a high affinity for leukocytes, leukocytes can be separated from blood products such as whole blood through capturing, adsorbing, attaching, or adhering leukocytes; it is important that the compound and polymer almost do not adsorb plasma proteins and hardly cause platelet attachment during the processes; therefore, the platelet retention rate is enhanced. Referring to FIG. 1, which illustrates two pathways for leukocyte depletion, path A and path B. Generally, the mechanism for leukocyte depletion is mainly through using a positively charged filter material F to adsorb plasma protein $P_1$, resulting in the attachment of platelets $P_2$. After activation of the attached platelets $P_2$, the cytokines and the growth factors are secreted as transmission signals and further cause the attachment of leukocytes L. Because platelets $P_2$ and leukocytes L are negatively charged, the surface of the filter material F is generally modified to have positive charges. However, using the positively charged filter material F tends to cause activation of platelets $P_2$, and it is not easy to simultaneously remove leukocytes and efficiently recover platelets $P_2$. The leukocyte depletion mechanism of the present invention (i.e., path B in FIG. 1) is different from the conventional mechanism (i.e., path A in FIG. 1), and the filter material F' prepared by using the embodiments of the invention can solve the problems of leukocyte depletion in the past. Accordingly, the present invention can effectively separate leukocytes, avoid activation of platelets or blood coagulation, and can also avoid increasing the concentration of bradykinin and the acute hypotensive reaction induced by bradykinin during blood transfusion.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

Figure 1:
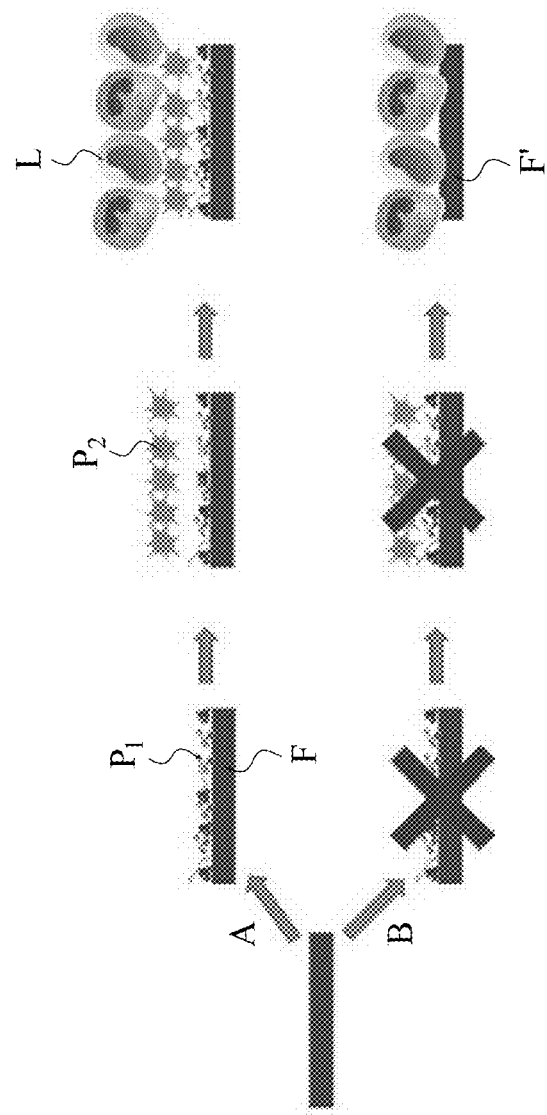
FIG. 1 is a schematic diagram illustrating the mechanism of leukocyte depletion in accordance with some embodiments of the present invention.

The representations of the symbols:

A pathway
B pathway
F filter material
F' filter material
L leukocyte
$P_1$ plasma protein
$P_2$ platelet
1 upper casing
2 filter material
3 lower casing

DETAILED DESCRIPTION

The following disclosure provides many different embodiments, or examples, for implementing different features of the provided subject matter. Specific examples of components and arrangements are described below to simplify the present disclosure. These are, of course, merely examples and are not intended to be limiting. For example, the formation of a first feature over a second feature in the description that follows may include examples in which the first and second features are formed in direct contact, and may also include examples in which additional features may be formed that are between the first and second features, such that the first and second features are not in direct contact. In addition, the present disclosure may repeat reference numerals and/or letters in the various examples. This repetition is for the purpose of simplicity and clarity and does not in itself dictate a relationship between the various examples and/or configurations discussed. In addition, the dimensions of the various features may be arbitrarily increased or reduced for clarity of discussion.

Further, spatially relative terms, such as "beneath," "below," "lower," "above," "upper" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. For example, if the devices in the figures are flipped, elements that are originally described as "under" or "below" other elements will become "above" these other elements. Therefore, the term "below" can encompass both the above orientation and the below orientation. The apparatus may be otherwise oriented (rotated 90 degrees or at other orientations), and the spatially relative descriptors used herein may likewise be interpreted accordingly.

The term "capture" refers to when the blood cells in a blood sample contact the surface of a material, the blood cells may be absorbed by the hydrophobic effect, hydrogen bonds, or electrostatic forces between the material and the blood cells, resulting in that the various blood cells may directly attach to the surface of the material, or the surface of the material first absorbs the smaller plasma proteins and platelets, resulting in the attachment of the larger blood cells; these processes are defined as "capture".

The term "separate" refers to that after a sample comprising leukocytes passes through a material for separating leukocytes, the leukocytes can be separated from the sample, i.e., the contents of leukocytes in the sample can be reduced, or even greatly reduced, thereby the leukocyte concentration in the filtrate after the separation is lower than the original sample comprising leukocytes. For example, samples comprising leukocytes and platelets can be separated to achieve a high recovery rate of platelets; alternatively, samples containing leukocytes and erythrocytes can be separated to achieve a high recovery rate of erythrocytes.

The term "leukocyte depletion" does not refer to that all or substantially all of the leukocytes are completely removed. The term is used to broadly indicate that the number of leukocytes is reduced during separation or filtration process.

The term "platelet concentrate" does not refer to limit a platelet concentrate into blood product, but the term broadly comprises a filtrate acquired from a cell suspension or a blood sample containing platelets treated with a separation material or a filter material. Wherein the volume of the filtrate may become larger or smaller than the volume of the cell suspension or the blood sample.

The term "leukocyte concentrate" broadly comprises a rinsing fluid which is buffer, solvent, or other solution after being used to rinse the species retaining in/on the separating material or filtration material after a cell suspension or blood sample comprising leukocytes is treated with the separating material or filtration material. The volume of the leukocyte-rich rinse may become larger or smaller than the volume of the cell suspension or the blood sample.

The term "erythrocyte concentrate" does not refer to limit erythrocyte concentrate into blood product, but the term broadly comprises a filtrate acquired from a cell suspension or blood sample containing erythrocytes treated with a separation material or a filter material. Wherein the volume of the filtrate may become larger or smaller than the volume of the cell suspension or the blood sample.

One aspect of the present invention is a polymer for capturing or separating leukocytes. The polymer can be used for manufacturing materials for capturing or separating leukocytes; alternatively, the polymer can be disposed on other materials, either alone or together with the other materials, for capturing or separating leukocytes.

The polymer is prepared by a polymerization reaction using an amide-hydroxyl-containing monomer, for example, a polymerization reaction completely using the amide-hydroxyl-containing monomer, or a polymerization reaction using the amide-hydroxyl-containing monomer with other compounds. It should be noted that any suitable materials can be used for this polymerization reaction. The suitable materials generally refer to any compound that has not yet been subjected to polymerization and is used to manufacture a polymer for capturing or separating leukocytes. In one example, the polymerization reaction may include an amide-hydroxyl-containing monomer, and the amide-hydroxyl-containing monomer has the structure of formula (I):

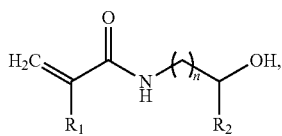

(I)

In formula (I), $R_1$ is independently selected from the group consisting of hydrogen, methyl group, ethyl group, hydroxyl group, one of from C1 to C12 carbon chain, and benzene ring; $R_2$ is independently selected from the group consisting of hydrogen, methyl group, ethyl group, one of from C1 to C6 carbon chain, amine group, and benzene ring; and n is an integer of 1 to 5.

In one example, the polymer is a copolymer copolymerized from the amide-hydroxyl-containing monomer with at least one other monomer. In one example, the polymer is a segmented polymer. In one example, the polymer is a crosslinked copolymer. In one example, the amide-hydroxyl-containing monomer is N-hydroxyethyl acrylamide, which may be called as N-(2-hydroxyethyl) acrylamide (HEAA). For example, the amide-hydroxyl-containing monomer has the structure of formula (I), wherein $R_1$ is hydrogen, $R_2$ is hydrogen, and n is 1, and the chemical structural formula is as follow:

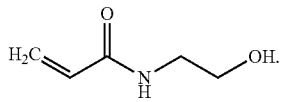

N-hydroxyethyl acrylamide is a compound having both a hydroxy functional group (—OH) and an amide functional group (—$R_n$C(O)$_x$NR'$_2$, wherein R and R' refer to a hydrogen atom or an organic group). In one example, the polymer may be simply polymerized from N-hydroxyethyl acrylamide monomers; alternatively, the polymer may be a copolymer copolymerized from N-hydroxyethyl acrylamide with other compounds.

The material for separating leukocytes comprises N-hydroxyethyl acrylamide monomers, has a high affinity for leukocytes, can specifically capture, adsorb, attach or adhere leukocytes, and hardly adsorbs plasma protein and attaches platelets (the specific experimental data will be described below in detail). As a result, the material for separating leukocytes of the present invention can effectively separate leukocytes. In addition, the materials for separating leukocytes can avoid activation of platelets or coagulation, avoid increasing the concentration of bradykinin and the acute hypotensive response induced by bradykinin during blood transfusion.

In some examples, the aforementioned polymerization reaction further comprises using a crosslinking agent, such as, but not limited to, using a crosslinking agent less than 10 wt %. The crosslinking agent is used to strengthen the mechanical properties of the hydrogel materials, and the crosslinking reagent does not relate to the blood compatibility of the material. The crosslinking agent can be mixed with an amide-hydroxyl-containing monomer (e.g., N-hydroxyethyl acrylamide monomer) to perform polymerization reaction. The crosslinking agent may be a monomeric compound or a polymer. In some examples, when the crosslinking agent is a monomeric compound, it is selected from the group consisting of N, N'-methylenebisacrylamide (NMBA) and ethylene glycol dimethacrylate (EGDMA). In some examples, when the crosslinking agent is a polymer, it is PLA-PEG-PLGA copolymer (PLA: Polylactic Acid, PEG: Polyethylene glycol, PLGA: Poly (lactic acid-co-glycolic acid), or poly(ethylene glycol) diacrylate (PEGDA). In some examples, the preferably selected crosslinking agent is NMBA, and the polymerization reaction is performed at a room temperature of 25° C.

The chemical structures of the crosslinking agents are as follows:

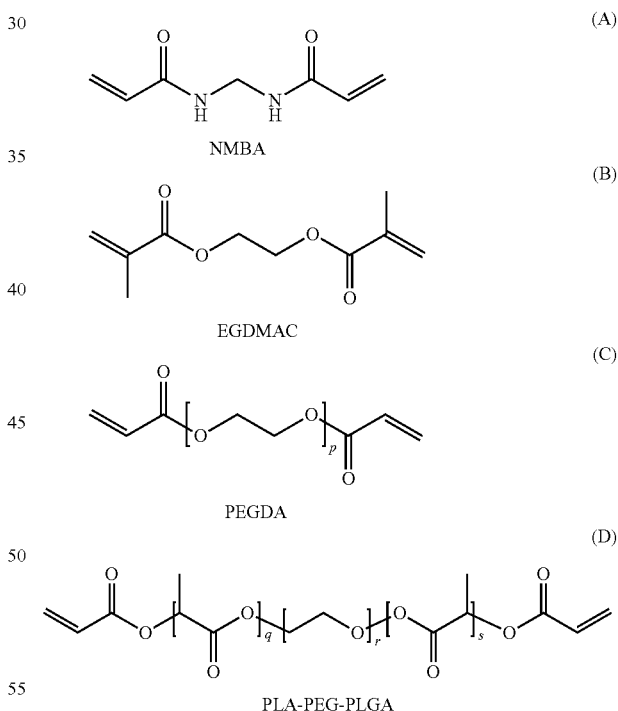

In some examples, the polymer for capturing or separating leukocytes can be hydrogel material, for example, a crosslinked polymer polymerized by a crosslinking reaction. In some examples of the present invention, the polymer may be a powder material, such as a segmented copolymer copolymerized with other monomers. The powder material can be dissolved in an alcohol solution to form a liquid and then be applied in coating, spraying, or impregnating. For specific examples of crosslinked polymers and copolymers, please refer to the following description.

In some examples, the aforementioned polymerization reaction further comprises using an initiator or a catalyst. For example, the aforementioned N-hydroxyethyl acrylamide monomer can be mixed with an initiator or a catalyst to accelerate the polymerization reaction. In some examples, the initiator is ammonium peroxodisulfate (APS). In some examples, the catalyst is N, N, N, N tetramethylethylenediamine (TEMED).

In one example, after completion of the polymerization reaction, the material for capturing or separating leukocytes can be cut or shaped according to desired sizes to have different shapes, such as membranous, plate-shaped, block-shaped, fibrous, tubular, beaded, granular, or powdery for following separation or filtration processes. It should be added that the separation or filtration process can be a continuous manner or a batch manner, for example, the material for separating leukocytes can be a filter membrane, a filter plate; alternatively, the material can be fiber, particle, or powder filled in a column.

One aspect of the invention is a device for capturing or separating leukocytes. The device includes a housing and a body. The body may be membranous, plate-shaped, block-shaped, fibrous, tubular, beaded, granular, or powdery, and the body includes a substrate and the above-mentioned polymer. Wherein the substrate is the main part of the shape of the body, and the polymer can be disposed on the substrate by coating, spraying, or impregnating; for example, the polymer is coated on one or both sides of a membranous substrate, or the substrate is completely impregnated in the polymer. Through the polymer, the body has the function of capturing or separating leukocytes, so that in some examples or embodiments, the body can be called as a filter material.

One aspect of the present invention is a device for capturing or separating leukocytes; the device comprises a housing and a body. In some examples, the body comprises a substrate and a polymer for capturing or separating leukocytes, the polymer is disposed on the substrate, and the polymer has a structure of formula (2):

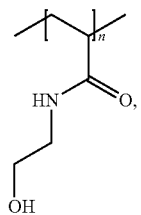

(2)

wherein n is an integer of 10 to 50. In some examples, the polymer can be hydrogel material. In some examples, the device for capturing or separating leukocytes can be a filter device.

Figure 2:
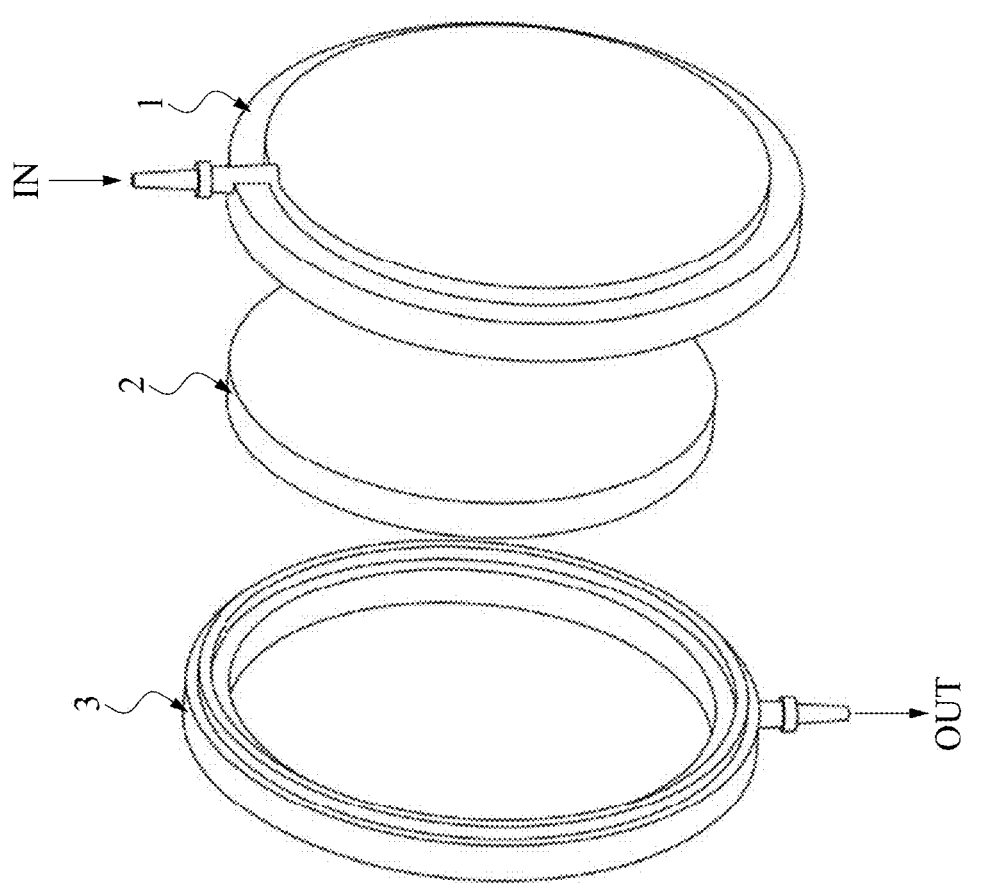
FIG. 2 illustrates a filter device for separating or capturing leukocytes in accordance with some embodiments of the present invention.

FIG. 2 shows a filter for capturing or separating leukocytes in accordance with some examples of the present invention. The housing includes an upper casing 1 and a lower casing 3, and the filter material 2 is located between the upper casing 1 and the lower casing 3. The filter can be a filter for separating leukocytes, a leukocyte-depleted platelet filter, or a leukocyte-depleted erythrocyte filter. Specifically, the filter for separating leukocytes is used for separating leukocytes from a blood sample. The leukocyte-depleted platelet filter is for passing a suspension sample containing leukocytes and platelets through the filter to separate the leukocytes from the platelets, thereby a high recovery rate of platelets is achieved. The leukocyte-depleted erythrocyte filter is for passing a suspension sample containing leukocytes and erythrocytes through the filter to separate the leukocytes from the erythrocytes, thereby a high recovery rate of erythrocytes is achieved. In one example, blood samples comprise whole blood samples, samples containing leukocytes and platelets, samples containing plasma protein, platelets or leukocytes, samples containing leukocytes or erythrocytes, or other samples containing cell suspension.

Before blood transfusion or prior to storage of plasma product, the filter material of the present invention can be used for pre-transfusion treatment or pre-storage treatment of plasma product to reduce the concentration of leukocytes in whole blood, platelet concentrate, or erythrocyte concentrate to a certain level (i.e., leukocyte depletion) to avoid or reduce adverse responses and comply with the regulations in various countries. For example, the American Association of Blood Banks (AABB) stipulates that the leukocyte content per unit of blood product must be less than $5 \times 10^6$; the prevailing European standard is that the leukocyte content per unit of blood product should be lower than $1 \times 10^6$.

The polymer in the filter material 2 can be obtained by mixing an amide-hydroxyl-containing monomer with a crosslinking agent and performing polymerization. In some examples, in the aforementioned filter for capturing or separating leukocytes, the polymer of the filter material 2 has the structure of formula (3):

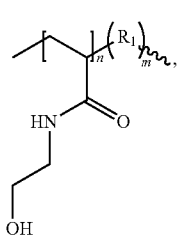

(3)

wherein m is an integer of 50 to 90, and $R_1=$

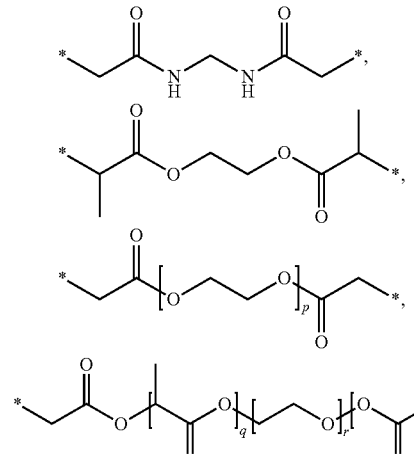

wherein p is an integer of 1 to 6, q is an integer of 1 to 6, s is an integer of 1 to 6.

The structure symbol "∽" used herein refers to an unbonded state. In other words, if a substituted group is connected to this symbol, it generally refers to that the substituted group can further connect to any other substituted group. The structural symbol "*" used herein refers to the connection position in the chemical structure of the substituted group.

The polymer in the filter material 2 can be obtained by mixing an amide-hydroxyl-containing monomer with an adsorption monomer and performing a polymerization reaction. In some examples, in the aforementioned filter for capturing or separating leukocytes, the polymer of the filter material 2 has the structure of formula (4):

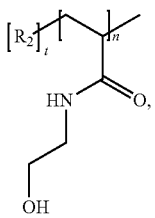

(4)

wherein t is an integer of 50 to 90.

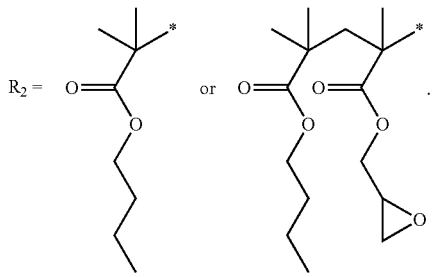 [SMILES: *C(C)(C)C(=O)OCCCC ; *C(C)(CC(C)(C)C(=O)OCCCC)C(=O)OCC1CO1]

In some examples, the filter material 2 may be a substrate with a modified membrane. For example, a polymer having the aforementioned formula (2), (3), or (4) is coated on the substrate to modify the surface of the substrate. In some examples, the elements on the modified surface of the substrate comprise carbon, oxygen, and nitrogen, and the total mole percentage of carbon, oxygen, and nitrogen is defined as 100%, wherein the mole percentage of carbon is from about 76.22% to about 79.84%, the mole percentage of oxygen is from about 18.1% to about 21.04%, and the mole percentage of nitrogen is from about 2.05% to about 2.75%.

One aspect of the present invention is the use of an amide-hydroxyl-containing polymer for capturing or separating leukocytes; the amide-hydroxyl-containing polymer comprises the structure of formula (2):

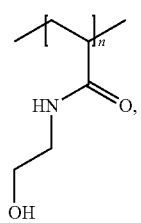

(2)

wherein n is an integer of 10 to 50.

For example, in some examples, the polymer containing the aforementioned structure of formula (2) is polymerized from N-hydroxyethyl acrylamide. The sample having leukocytes pass through a material containing N-hydroxyethyl acrylamide; therefore, N-hydroxyethyl acrylamide can specifically capture, adsorb, attach, or adhere leukocytes. In another example, the use of separating leukocytes is contacting a sample having leukocytes with the material for capturing or separating leukocytes, and the method of contacting may be flowing through, filtering, or batch contacting; after the contacting, the liquid can be collected or removed from the material for capturing or separating leukocytes. By using the polymer containing the aforementioned formula (2), the capture rate of leukocytes can be at least 87%.

One aspect of the invention is the use of the aforementioned amide-hydroxyl-containing monomer of formula (1); the use is for manufacturing a filter material for capturing or separating leukocytes.

In some examples, the step of manufacturing a filter material for capturing or separating leukocytes comprises providing a substrate and modifying the substrate with an amide-hydroxyl-containing monomer. The substrate may be membranous, plate-shaped, block-shaped, fibrous, tubular, beaded, granular, or powdery substrates. Depending on the use and requirements of the capturing or separating process, the amide-hydroxyl-containing monomer is used to modify the surface of a substrate. For example, a coating material polymerized from N-hydroxyethyl acrylamide monomers or N-hydroxyethyl acrylamide monomers with another compound is coated on the surface of the substrate. It should be added that the following separation or filtration process can be a continuous way or a batch way, for example, the filter material for capturing or separating leukocytes can be a filter membrane, filter plate; alternatively, the filter material can be fiber, particle or powder filled in a column. In some examples, the substrate is polypropylene or polyethylene terephthalate.

Further, the method for modifying the surface of the substrate may be a physical modification or a chemical modification. Physical modification method includes coating, which is a modification of the surface properties of the material by physical force, and the adsorption force of coating includes van der Waals forces, hydrogen bonding, hydrophobic interactions, electrostatic interactions, and the like. Chemical modification method includes grafting or etching; grafting method is modifying the surface properties of the material by chemical bonding, and chemical grafting method comprises ozone-initiated, ultraviolet light-initiated, or plasma-initiated free radical polymerization. In addition, the surface property of the material may be modified by a combination of a coating method and a grafting method; first, the monomers of the material or the copolymer may be adsorbed on the surface of the substrate by coating, and then chemical grafting is performed by ozone, ultraviolet light, or plasma treatment. Preferably, the surface modification method is coating, grafting, or a combination thereof.

In some examples, physical modification method is used to perform the surface modification. For example, modifying the substrate with amide-hydroxyl-containing monomers comprising the following steps. First, about 20 to about 40 parts by weight of the amide-hydroxyl-containing monomers is provided, and about 60 to about 80 parts by weight of adsorbent monomers is provided. Next, the polymerization of the amide-hydroxyl-containing monomers and the adsorbent monomers is performed to form a copolymer. Finally, the copolymer is coated on the surface of the substrate. In some examples, the adsorbent monomer is selected from the group consisting of butyl methacrylate, glycidyl methacrylate, and a combination thereof.

In some examples, chemical modification is used to perform the surface modification. For example, modifying the substrate with the amide-hydroxyl-containing monomers comprises the following steps. The amide-hydroxyl-containing monomers are coated on the substrate. Next, the graft reaction is performed by treating the substrate and the amide-hydroxyl-containing monomers on the substrate with ultraviolet rays. It should be understood that additional operations may be used in this embodiment, and the operations may be replaced or deleted, or the orders of the operations may be alternated. In another example, modifying the substrate with amide-hydroxyl-containing monomer comprises: the substrate is treated with ultraviolet light; and the amide-hydroxyl-containing monomers are coated on the substrates treated with the ultraviolet light to perform grafting reaction.

In order to confirm the effect of capturing or separating leukocytes for the embodiments of the present invention, the following tests were carried out. It should be noted that the following examples are provided only for illustrative purpose and are not intended to limit the invention.

EXPERIMENTAL METHODS AND MATERIALS

1. The Experiments of Hydrogels
1.1 Experimental Materials for Hydrogel Preparation The first structure type is monomers only having hydroxyl group, 2-hydroxyethyl acrylate (HEA) and 2-hydroxyethyl methacrylate (HEMA), and the chemical structures are respectively as follows:

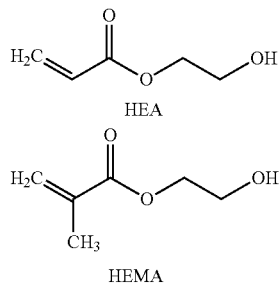

The second structure type is monomers only having amide group, acrylamide (AAm) and methacrylamide (MAA), and the chemical structures are respectively as follows:

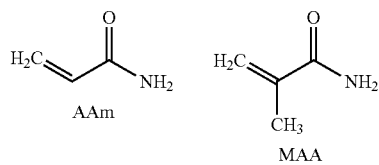

The third structure type is monomers having both hydroxyl group and amide group, N-(2-hydroxypropyl) methacrylamide (HPMA), and N-hydroxyethyl acrylamide (also called as N-(2-Hydroxyethyl) acrylamide, HEAA), and the chemical structures are respectively as follows:

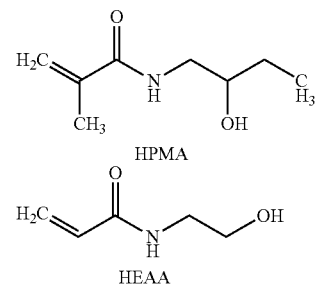

The fourth structure type is zwitterionic compounds, which are ([3-Methacryloylamino)propyl]dimethyl (3-sulfopropyl) ammonium hydroxide (SBAA) and [2-(methacryloyloxy)ethyl]dimethyl-(3-sulfopropyl) ammonium hydroxide (SBMA), and the chemical structures are respectively as follows:

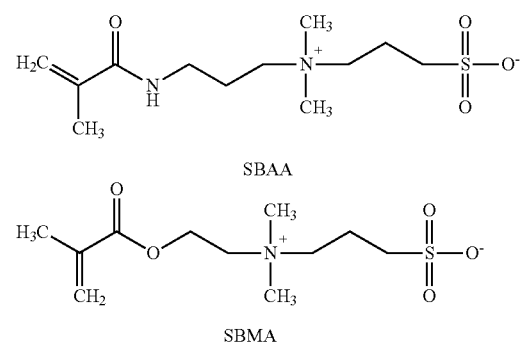

Ammonium peroxodisulfate (APS) was used as an initiator in the test and has the following chemical structure:

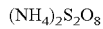

N, N, N, N tetramethylethylenediamine (TEMED) was used as a catalyst in the test and has the following chemical structure:

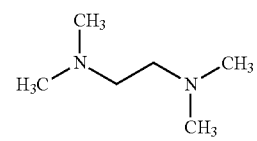

The crosslinking agent used in the test is N, N'-Methylenebisacrylamide (NMBA), and the chemical structure is as shown in the foregoing discussion and not mentioned again here.

1.2 Preparation of Hydrogel Materials
1.2.1 Hydrogels Having Amide Groups

In this step, two hydrogels having amide groups, namely acrylamide (AAm) hydrogel and methyl acrylamide (MAA) hydrogel, are provided. First, AAm and MAA were respectively dissolved in deionized water and the crosslinking agent NMBA was added respectively. The AAm solution was stirred in an ice bath for 10 minutes, and the MAA solution was stirred at room temperature for 10 minutes. After the AAm and MAA were uniformly mixed with the crosslinking agent NMBA respectively in the ice bath and at room temperature, the initiator was added to react for 10 minutes, and then the catalyst TEMED was added. Next, the aforementioned mixtures were respectively sucked into glass molds by syringes, and then free radical crosslinking polymerization was carried out at room temperature for 1 hour to form the hydrophilic hydrogels.

1.2.2 Hydrogels Having Hydroxyl Groups

In this step, two hydrogels having hydroxyl groups, namely hydroxyethyl acrylate (HEA) hydrogel and hydroxyethyl methacrylate (HEMA) hydrogel, are provided. First, HEA and HEMA were respectively dissolved in methanol, then a crosslinking agent NMBA was added, and the mixtures were stirred for 10 minutes respectively. After HEA and HEMA were uniformly mixed with the crosslinking agent NMBA respectively, the initiator APS was added to react for 10 minutes, and then the catalyst TEMED was added. Next, the solutions were sucked into glass molds by syringes, and free radical crosslinking polymerization was carried out at room temperature for 1 hour to form the hydrophilic hydrogels.

1.2.3 Hydrogels Having Both Hydroxyl Groups and Amide Groups

In this step, two hydrogels having both hydroxyl groups and amide groups, namely N-(2-hydroxypropyl) methacrylamide (HPMA) hydrogel and N-hydroxyethyl acrylamide (HEAA) hydrogel, are provided. First, HPMA and HEAA were respectively dissolved in deionized water, NMBA was added, and the mixtures were stirred for 10 minutes respectively. After HPMA and HEAA were uniformly mixed with the crosslinking agent NMBA respectively, the initiator APS was added to react for 10 minutes, and then the catalyst TEMED was added. Next, the solutions were sucked into glass molds by syringes, and free radical crosslinking polymerization was carried out at room temperature for 1 hour to form the hydrophilic hydrogels.

1.2.4 Zwitterionic Hydrogels

In this step, two zwitterionic hydrogels, namely [3-(methacrylamido)propyl]dimethyl(3-thiopropyl)ammonium hydroxide (SBAA) hydrogel and [2-(Methacryloyl)ethyl]dimethyl-(3-sulfonylpropyl)ammonium hydroxide (SBMA) hydrogel, are provided. First, SBAA and SBMA were respectively dissolved in deionized water, then crosslinking agent NMBA was added, and the mixtures were stirred for 10 minutes respectively. After SBAA and SBMA were uniformly mixed with the crosslinking agent NMBA, the initiator APS was added to react for 10 minutes, then the catalyst TEMED was added, the solutions were sucked into glass molds by syringes, and free radical crosslinking polymerization was performed at room temperature for 1 hour to form the zwitterionic hydrogels.

1.3 Measurement of Hydration Ability

The hydrophilic polymer dissolved in an aqueous solution can form a hydration layer by capturing the water molecules in the aqueous solution through hydrogen bonds or ionic bonds (zwitterionic polymer); the hydration layer not only reduces the free energy of the contact interface between the material and biomolecules, but also creates a physical barrier preventing approach and attachment of proteins; thereby attachment of biomolecules such as proteins can be avoided (Reference: Morisaku, T., J. Watanabe, T. Konno, M. Takai and K. Ishihara: Hydration of phosphorylcholine groups attached to highly swollen polymer hydrogels studied by thermal analysis. Polymer, 2008.49(21): p. 4652-4657. Chen, S., L. Li, C. Zhao and J. Zheng: Surface hydration: Principles and applications toward low-fouling/nonfouling biomaterials. Polymer, 2010.51(23): p. 5283-5293.) The overall hydrophilicity of a material can be determined by the equilibrium water content of the material; the higher the equilibrium water content, the more hydrophilic the material is. The hydrogels were respectively soaked in deionized water and phosphate buffered saline (PBS), and the soaking solutions were replaced every 30 minutes and repeated 3 times to ensure the methanol in the hydrogel was replaced. Then, the hydrogels were respectively soaked in deionized water and PBS and placed in an oven at 37° C. for 24 hours, and then after the excess water on the surfaces of the hydrogels was removed, the wet weight (Ww) of each of the hydrogels was measured. Next, the hydrogels were transferred to a new 24-well plate and placed in a vacuum oven and evacuated for 24 hours, and then the dry weight (WD) of each of the hydrogels was measured. Equilibrium water content (EWC) can be calculated through the following equation (I):

$$\text{Equilibrium water content} = \frac{W_W - W_D}{W_W} \cdot 100\% \tag{1}$$

The strength of hydration ability affects the degree to which a hydrophilic polymer material forms a hydration layer and indirectly affects the effect of the material against biomolecular adhesion or protein adsorption. Although the relationship between a polymer material and water molecules at a macroscopic scale can be obtained from equilibrium water content, the affinity relationship between a polymer material and water molecules cannot be explained at a microscopic scale; therefore, the following experiments were carried out for finding further supports.

1.4 Analysis of States of Water Molecules

At a microscopic scale, when water molecules are in contact with hydrophilic polymer structures, three different states of water molecules are generated: (1) nonfreezable bound water; nonfreezable bound water and the polymer form a strong interaction force, and nonfreezable bound water does not form ice crystals even at −100° C.; according to the literature, nonfreezable bound water is the main factor for resisting the adhesion of biomolecules; (2) freezable bound water; freezable bound water is located on outside of the nonfreezable bound water; freezable bound water intermittently acts with the polymer or the nonfreezable bound water, and the temperature for freezable bound water to form ice crystals is below 0° C. (3) free water; free water is located on the outside of the freezable bound water; free water is very slightly or even unaffected by the polymer or the nonfreezable bound water; therefore, similar to normal water, free water forms ice crystal at 0° C. (Reference: Higuchi, A. and T. Iijima: D.s.c. investigation of the states of water in poly(vinyl alcohol-co-itaconic acid) membranes. Polymer, 1985.26(12): p. 1833-1837. Higuchi, A. and T. Ijima: D.s.c. investigation of the states of water in poly(vinyl alcohol-co-itaconic acid) membranes. Polymer, 1985.26(8): p. 1207-1211. Tanaka, M. and A. Mochizuki: Effect of water structure on blood compatibility-thermal analysis of water in poly (meth) acrylate. Journal of Biomedical Materials Research Part A, 2004.68(4): p. 684-695.)

The differential scanning calorimetry (DSC) can be used to measure the amount of enthalpy change ($\Delta Hf$) in hydrogels to determine the states of the water molecules; therefore, the contents of different states of the water molecules can be further identified. (Reference: Tanaka, M. and A. Mochizuki: Effect of water structure on blood compatibility-thermal analysis of water in poly (meth) acrylate. Journal of Biomedical Materials Research Part A, 2004.68(4): p. 684-695.) The higher proportion of nonfreezable bound water formed around the polymer indicates that there is a stronger hydration ability at a microscopic scale, the formed hydration layer is denser, and the polymer should have higher ability to resist adhesion of biomolecules or adsorption of proteins (Reference: Morisaku, T., J. Watanabe, T. Konno, M. Takai and K. Ishihara: Hydration of phosphorylcholine groups attached to highly swollen polymer hydrogels studied by thermal analysis. Polymer, 2008.49(21): p. 4652-4657.)

The hydrogels were respectively placed in deionized water, and the soaking solutions were replaced every 30 minutes and repeated 3 times to ensure that the methanol in the hydrogels was replaced. Then, the hydrogels were soaked in deionized water for 1 day and the excess water on the surfaces of the hydrogels was removed; 3~4 mg of each of the hydrogels was taken and placed in a specific aluminum plate for differential scanning calorimetry (DSC), and the DSC temperature range and condition were set to be cooled from 25° C. to −40° C., and then the temperature was raised 5° C. per minutes until 40° C.

The integral area under the endothermic peak curve is calculated as the endothermic enthalpy change (ΔHf) of the phases change during melting of ice crystal, and the general endothermic enthalpy (ΔHw) during melting of ice is 333.5 J/g. The weight percentage of freezable bound water ($w_{freezable}$) is calculated by the following equation (2):

$$W_{freezable} = \frac{\Delta H_f}{\Delta H_w} \cdot 100\% \quad (2)$$

Further, it has known that equilibrium water content is composed of nonfreezable bound water and freezable bound water; therefore, the weight percentage of nonfreezable bound water ($w_{nonfreezable}$) can be acquired according to the following equation (3) and equation (4):

$$EWC = w_{nonfreezable} + w_{freezable} \quad (3)$$

$$w_{nonfreezable} = EWC - w_{freezable} \quad (4)$$

The unit weight of nonfreezable bound water and freezable bound water per unit weight of hydrogel polymer can be obtained by the following equation (5) and equation (6), wherein $w_{polymer}$ is the weight percentage of the polymer in the hydrogel:

$$W_{nonfreezable} = \frac{W_{nonfreezable}}{W_{polymer}} \quad (5)$$

$$W_{freezable} = \frac{W_{freezable}}{W_{polymer}} \quad (6)$$

$W_{nonfreezable}$ is the ratio of nonfreezable bound water can be formed by polymer chains (g H2O/g polymer). Then, the number of moles of nonfreezable bound water bonded per mole of the polymer repeating unit, which is represented as dimensionless group Nw, can be converted by the following equation. $M_p$ is the molecular weight of each repeat unit of the polymer, and $M_w$ is the molecular weight of water:

$$N_W = W_{nonfreezable} \cdot \frac{M_p}{M_w} \quad (7)$$

1.5 the Enzyme-Linked Immunosorbent Assay (ELISA)

The various hydrogels prepared as described above were separately placed in deionized water and PBS, and the PBS was changed every 30 minutes and repeated three times to ensure that the methanol in the hydrogels was replaced. Then the hydrogels were transferred to a 24-well plate (24 well-tissue culture polystyrene plate, i.e., 24-well TCPS plate) and washed three times with PBS. 1 ml of PBS was added in each of the hydrogel samples and the vacant TCPS wells, then the hydrogels were soaked at 37° C. in an oven for 2 hours, and then the PBS was removed.

The target proteins to be tested (HSA, γ-globulin, and fibrinogen) or poor platelet plasma (PPP) was added to each of the hydrogel samples, wherein the concentration of a single protein was 1 mg/ml. After the hydrogels were placed in an oven at 37° C. for 30 minutes, the target proteins to be tested (or PPP) were removed, the hydrogels were washed three times with PBS, and then the solutions were removed.

1 ml of 1 mg/ml bovine serum albumin (BSA) was added to each of the hydrogel samples, and the samples were placed in an oven at 37° C. for 30 minutes to fill the parts unadsorbed by the target proteins on the hydrogel samples, then the PBS was used to wash the hydrogel samples for three times to remove the excess BSA.

A first antibody (1st antibody) specific for each of the target proteins was added to each of the hydrogel samples, the samples were placed in an oven at 37° C. for 30 minutes, then the hydrogel samples were washed three times with PBS, and then the solutions were removed.

1 ml of 1 mg/ml BSA was added to each of the hydrogel samples, the hydrogel samples were placed in an oven at 37° C. for 30 minutes, then the hydrogel samples were washed three times with PBS, and then the solutions were removed.

1 ml of secondary antibody (2nd antibody) was added to each of the hydrogel samples; the 2nd antibody is specific and binds only to the first antibody; the hydrogel samples were placed in an oven at 37° C. for 30 minutes, then the hydrogel samples were washed 5 times with PBS, and then the solutions were removed (this step is not required in the measurement of γ-globulin adsorption).

After the PBS was removed, the hydrogel samples were placed in new 24-well TCPS plates, 0.5 ml of developer, 3,3',5,5'-Tetramethylbenzidine (TMB), was added to each of the hydrogel samples; after 6 minutes of color development, 0.5 ml of 1 M sulfuric acid was added to each of the hydrogel samples to terminate the reaction. 200 μl of the solution was pipetted from each of the hydrogel samples (also from vacant TCPS wells) into a 96-well plate, and by a microplate reader (Bio-tek Model PowerWare XS), the reading values of UV wavelength of 450 nm were used to calculate back the protein absorption degrees for the hydrogel samples.

1.6 Attachment Test of Blood Cells

Each of the prepared hydrogels was respectively soaked in PBS, and the PBS was replaced every 30 minutes and repeated 3 times to ensure that the methanol in the hydrogels was replaced. Then the hydrogels were soaked in PBS and placed in an oven at 37° C. for 1 day. The PBS was removed, and 1 ml of platelet concentrate and leukocyte concentrate were respectively added to the hydrogels, and then the hydrogels were placed in an oven at 37° C. for 30 minutes. Then the hydrogels were washed with PBS to remove the unattached blood cells. 2.5 wt % glutaraldehyde solution was added to the 24-well plate, and the hydrogels were placed in a refrigerator at 4° C. for 1 day to fix the blood cells. On the next day, a conjugated laser scanning microscope (CLSM, Nikon model A1R) was used to observe the attachment of the blood cells, and the numbers of attached blood cells per unit area were calculated.

Figure 3:
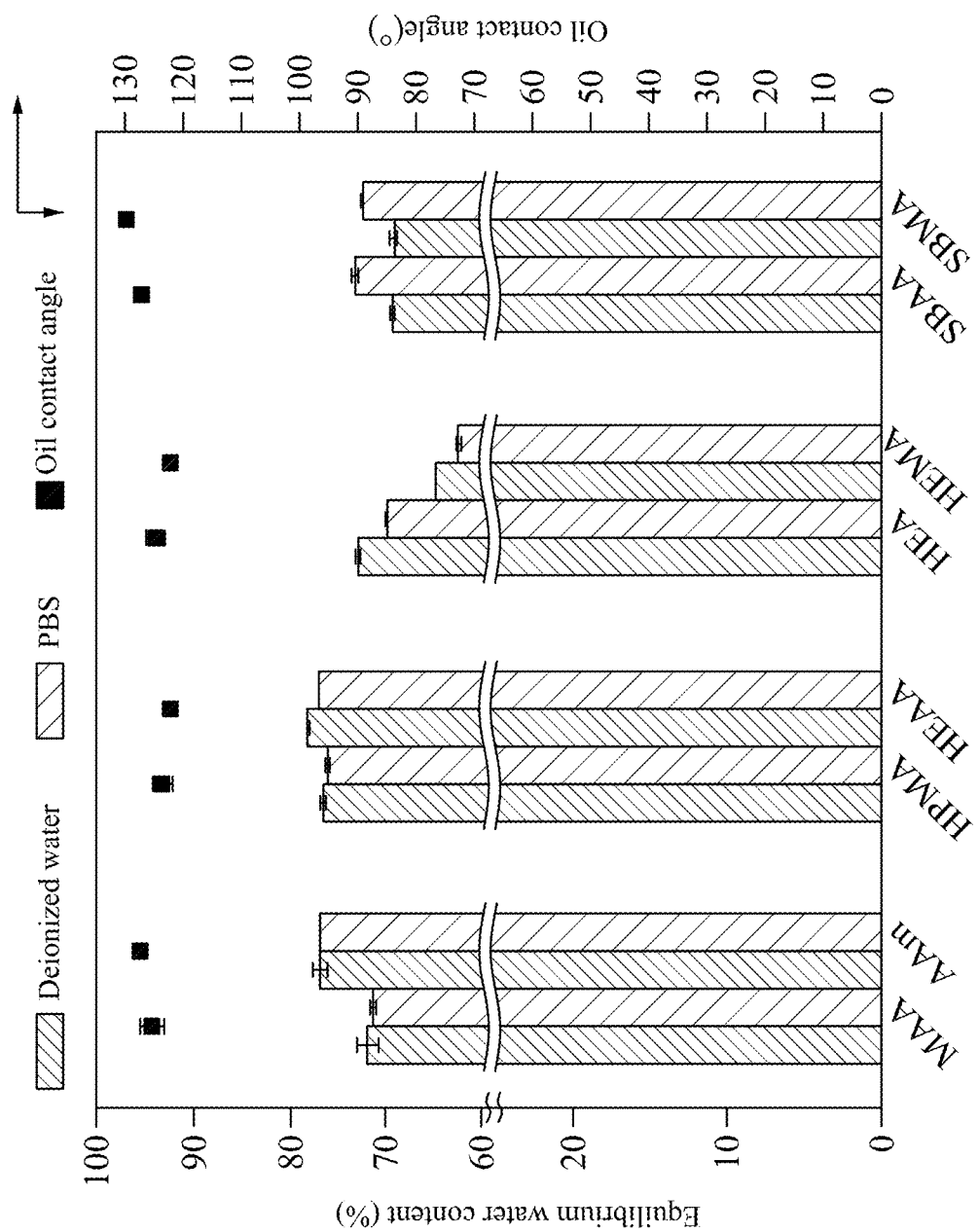
FIG. 3 illustrates the results of equilibrium the water contents and the oil contact angles of the various hydrogel materials in accordance with some embodiments of the present invention.

2. The Detection Results of Hydrogel Materials 2.1 Analysis of the Equilibrium Water Content of the Hydrogels As shown in FIG. 3, the abscissa represents the various hydrogels, and the ordinate represents the equilibrium water content (%). First, compared to the hydrophilic hydrogels in PBS, the hydrophilic hydrogels (AAm, MAA, HEA, HEMA, HPMA, and HEAA) had higher equilibrium water contents in deionized water; this is because the amide groups or the hydroxyl groups in the hydrophilic hydrogels can fully form hydrogen bonds with water molecules, and the ionic force between the salt in PBS and the water molecules competes with the hydrogen bonding of the hydrophilic hydrogels, resulting in the lower equilibrium water contents of the hydrophilic hydrogels in PBS than those in deionized water solution. Second, compared to the zwitterionic hydrogels in PBS, the equilibrium water contents of the zwitterionic hydrogel (SBAA and SMBA) were lower in deionized water; this is because the positive and negative charges in the structure of the zwitterionic hydrogels capture water molecules through ionic bonding, the zwitterionic hydrogel can resist the ionic bonding of the salt ions of PBS; therefore, the zwitterionic hydrogels have higher equilibrium water contents in PBS. In addition, the order of hydrogels according to the equilibrium water contents of the hydrophilic hydrogels from low to high was hydrogels having hydroxyl groups (HEA, HEMA), hydrogels having amide groups (AAm, MAA), and hydrogels having both hydroxyl groups and amide groups (HPMA, HEAA). Accordingly, hydrogels having amide groups are more hydrophilic than hydrogels having hydroxyl groups; therefore, if hydrogels comprise hydroxyl groups and further comprise amide groups, the hydrogen bonding sites can be increased. Therefore, the equilibrium water contents of the hydrogel having HPMA monomers and the hydrogel having HEAA monomers were the highest.

2.2 Analysis of the States of Water Molecules for the Hydrogels

Figure 4:
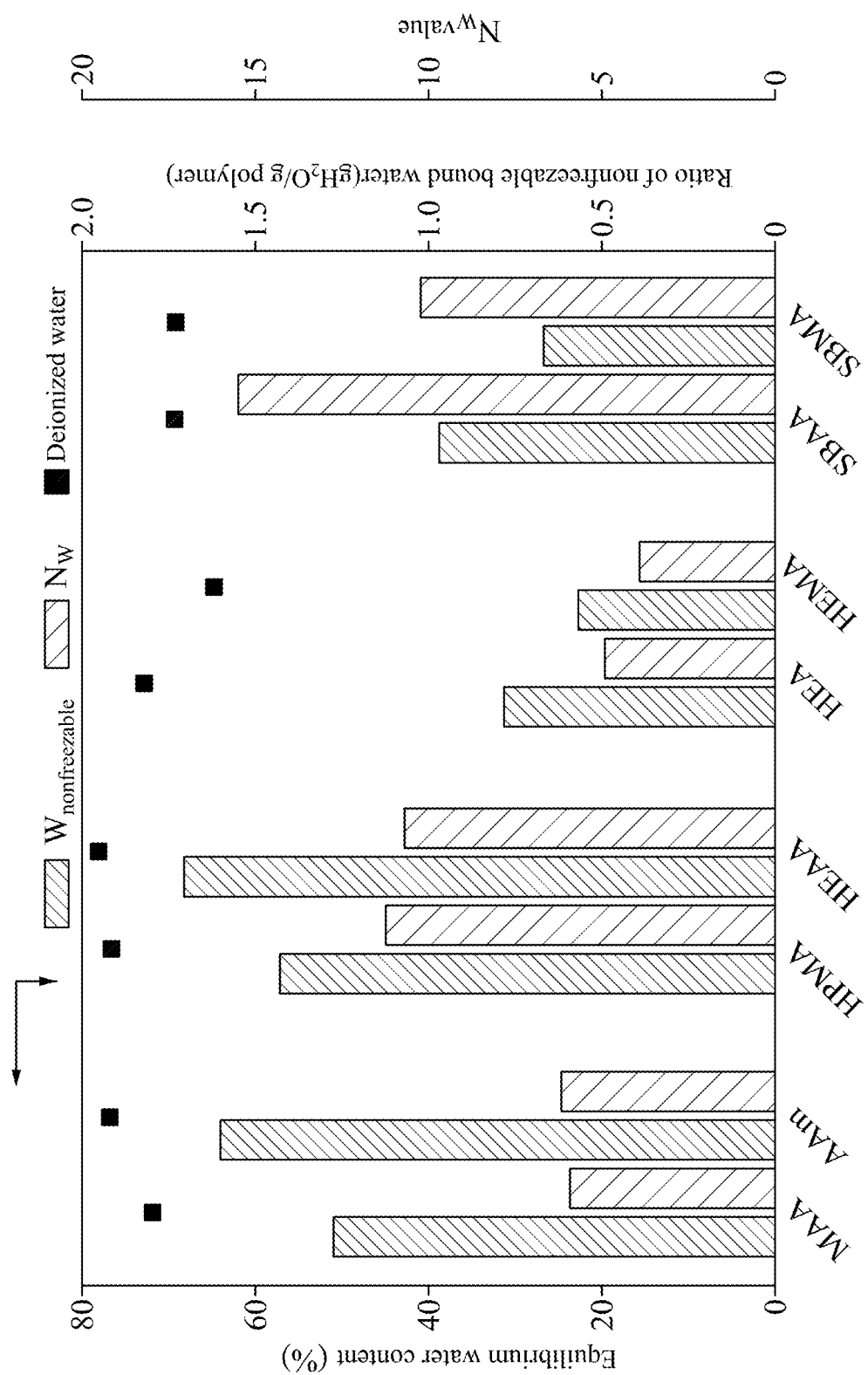
FIG. 4 illustrates the results of the equilibrium water contents, the ratios of nonfreezable bound water, and the dimensionless groups of the various hydrogel materials in accordance with some embodiments of the present invention.

FIG. 4 shows the equilibrium water contents, the ratios of nonfreezable bound water, and the dimensionless groups of various hydrogels in deionized water. The abscissa represents the various hydrogels, the left ordinate represents the equilibrium water content (%), and the right ordinate respectively corresponds to the ratio of nonfreezable bound water ($gH_2O$/g polymer) and the dimensionless group $N_w$.

The nonfreezable bound water content is represented as Wnonfrezzable; among the hydrophilic hydrogels, the nonfreezable bound water contents of the hydrogels having amide groups (AAm, MAA) were higher than those of hydrogels having hydroxyl groups (HEA, HEMA); because an amide group is both a hydrogen bond acceptor and a hydrogen bond donor, an amide group has higher bonding ability and bonding probability of water molecules compared to a hydroxyl group, which is only a hydrogen bond acceptor. Accordingly, the hydrogels having HPMA monomers and HEAA monomers can provide more hydrogen bonding sites because they have both hydroxyl groups and amide groups; therefore, more water molecules are bonded around the polymer chain to form denser hydration layers.

It should be noted that since it is difficult to calculate the molecular weight and the degree of polymerization in a hydrogel system, the dimensionless group NW is used, and the physical meaning thereof is the number of moles of nonfreezable bound water boned per mole of the repeating unit of polymer; therefore, the higher the NW value, the more nonfreezable bound water formed from per mole of monomers. The order of hydrogels according to NW values from high to low was zwitterionic hydrogels (SBAA, SBMA), hydrogels having both hydroxyl groups and amide groups (HPMA, HEAA), hydrogels having amide groups (AAm, HEMA), hydrogels having hydroxyl groups (HEA, HEMA). Because of the positive and negative charges in the chemical structures of zwitterionic hydrogels, the generated ionic force is very strong, resulting in excellent hydrophilicity and hydration ability of zwitterionic hydrogels. However, the hydrogel having HPMA monomers and the hydrogel having HEAA monomers have hydroxyl groups and amide groups which can enhance the sites and probability of hydrogen bonding of water molecules; therefore, the hydration ability of such hydrogels is not less than that of zwitterionic hydrogels.

2.3 Adsorption Between the Hydrogel and Single Plasma Protein

Common plasma proteins are human serum albumin (HSA), immunoglobulin (Ig), and fibrinogen; among them, immunoglobulins can be further divided into IgA, IgD, IgE, IgG, and IgM, and most of IgGs are γ-globulin. In addition to closely related to the immune system, the structure of γ-globulin has saccharide residues which can interact with the glycosyltransferase of platelets, resulting in platelet aggregation. Therefore, in this experiment, HSA, γ-globulin, and fibrinogen were used as target proteins to observe the adsorption effect of the hydrogels on the target proteins in plasma proteins.

Figure 5:
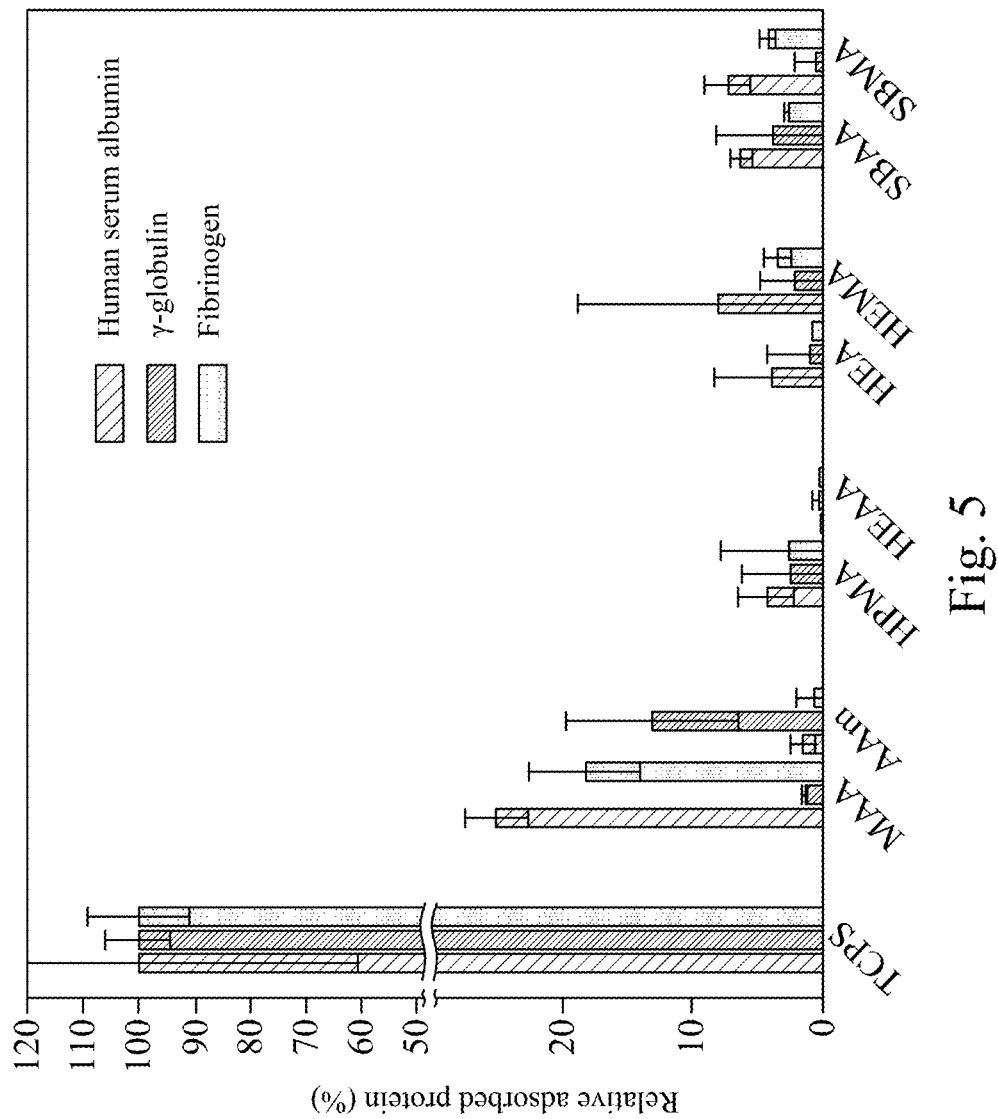
FIG. 5 illustrates the results of the relative protein adsorption for the various hydrogels in enzyme-linked immunosorbent assay (ELISA) in accordance with some embodiments of the present invention.

In this experiment, after 1 mg/ml HSA, γ-globulin, and fibrinogen were respectively prepared, protein absorption was measured by ELISA; because the protein solution of each reactive adsorption test by ELISA contained only one kind of protein, no other protein competes in adsorption reaction in the environment, the maximum amounts of adsorbed protein for different hydrogel materials can be presented. As shown in FIG. 5, the abscissa represents the various hydrogels, and the ordinate represents the amount of relative adsorbed protein. The amounts of relative adsorbed plasma protein for hydrogels having hydroxyl groups (HEA, HEMA), hydrogels having amide groups (AAm, MAA), hydrogels having both hydroxyl groups and amide groups (HPMA, HEAA), and zwitterionic hydrogels (SBAA, SBMA) were all below 10%. It is noted that the amounts of adsorbed HSA, γ-globulin, or fibrinogen for hydrogel having HEAA monomers were quite low, much less than 3%, and even the adsorption ratios were close to 0.

2.4 Adsorption or Attachment Between Hydrogel and Fibrinogen or Platelet

Figure 6:
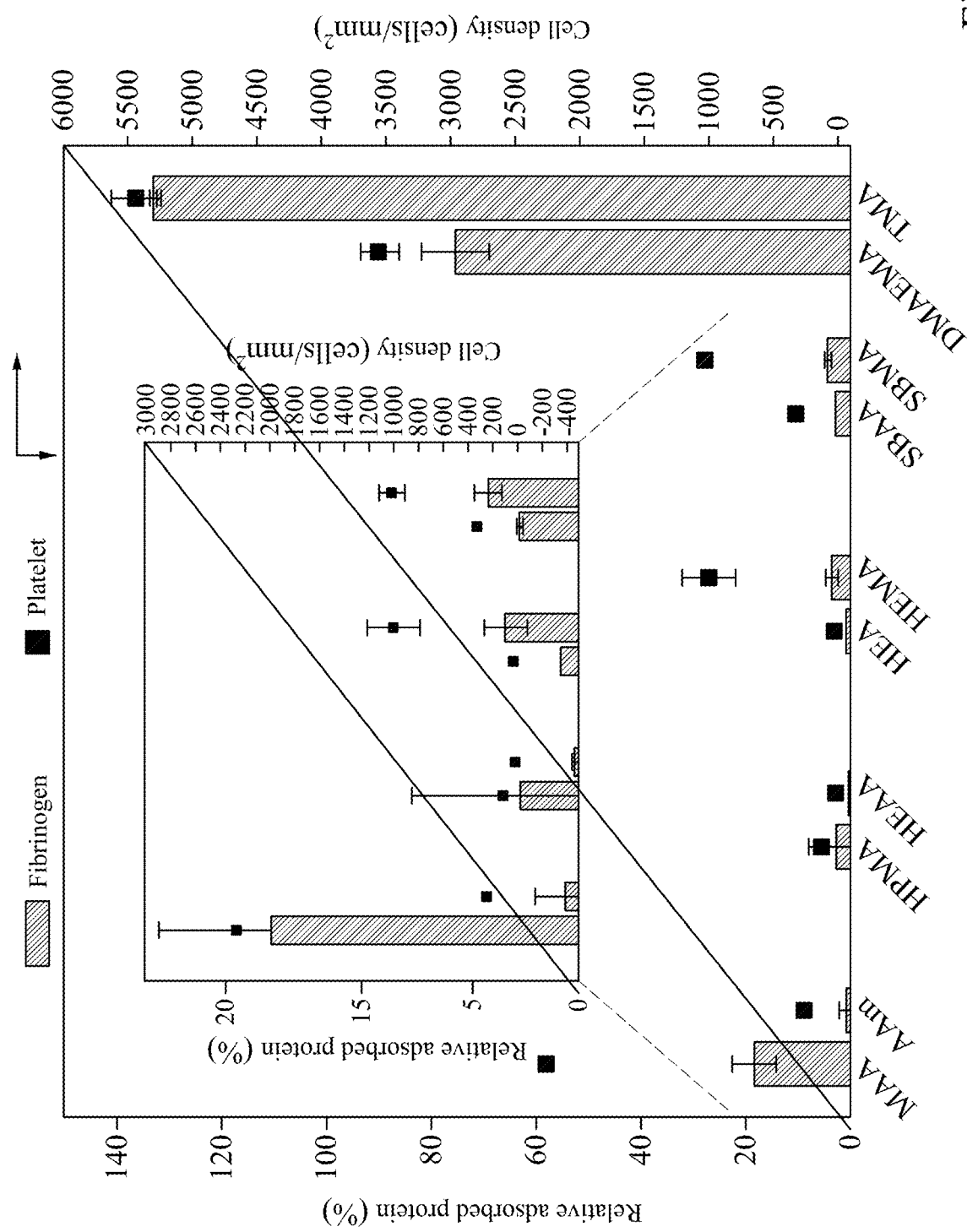
FIG. 6 illustrates the results of the amounts of adsorbed protein and the cell densities on the surfaces of the various hydrogel materials in accordance with some embodiments of the present invention.

In this experiment, 1 mg/ml fibrinogen and 1 ml platelets were used for adsorption experiments. As shown in FIG. 6, the abscissa represents the various hydrogels, the amounts of relative adsorbed fibrinogen correspond to the left ordinate, and the cell densities of platelets (cells/$mm^2$) correspond to the right ordinate. In addition, in order to make the differences between the values be more clearly presented, the small graph in the figure is a magnified graph of the part indicated by the dotted line.

N,N-dimethylaminoethyl methacrylate (DMAEMA) and Trimellitic anhydride (TMA) are two hydrogels having positive charges and have high amounts of adsorbed fibrinogen and high numbers of attached platelets because of the negative charges on the surface of platelets; therefore, contacting platelets with DMAEMA hydrogel and TMA hydrogel cause irreversible adsorption due to electrostatic force, and a large number of platelets are adsorbed. The amounts of adsorbed fibrinogen and the numbers of attached platelets for the hydrogels having hydroxyl groups, the hydrogels having amide groups, the hydrogels having both hydroxyl groups and amide groups, and the zwitterionic hydrogels of the present invention were all quite low, even much lower than the amounts of adsorbed fibrinogen and the numbers of attached platelets for DMAEMA hydrogel and TMA hydrogel. It is noted that the amounts of adsorbed fibrinogen for hydrogels having HEAA monomers were less than 3% (preferably less than 2%, more preferably less than 1%), and in FIG. 6, the amounts of adsorbed fibrinogen and the numbers of attached platelets were even close to 0. Therefore, the hydrogel having HEAA monomers hardly adsorbs fibrinogen, and further hardly attaches platelet; therefore, platelet activation can be reduced. The reduction in platelet activation, in turn, reduces the clotting reaction during contacting with blood; therefore, it is not necessary to add an anticoagulant in the process of recovering platelets. In addition, conventionally known filter material having electrically charged surfaces tends to increase the concentration of bradykinin. Using hydrogel having HEAA monomers without surface charge can also avoid the acute hypotensive reaction due to an increase in the concentration of bradykinin during blood transfusion.

2.5 Adsorption or Attachment Between Hydrogel and Leukocytes

Figure 7:
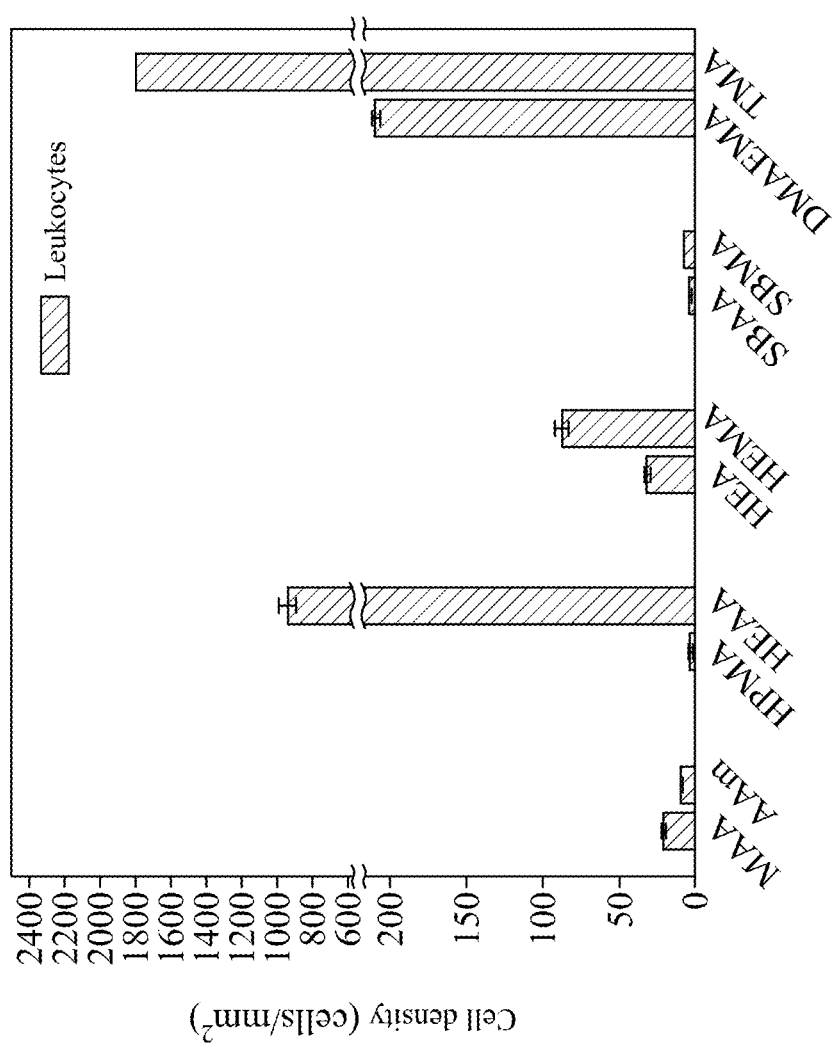
FIG. 7 illustrates the results of the numbers of attached leukocytes for the various hydrogels in accordance with some embodiments of the present invention.

In this experiment, leukocyte concentrate was used to perform leukocyte adsorption or attachment experiments, and the fluorescent signals from the leukocytes attached to the surface of the hydrogels were observed by a conjugated laser scanning microscope (CLSM), and the numbers of fluorescent signals of the leukocytes were calculated. The results are shown in FIG. 7; the numbers of attached leukocytes for the hydrogels having amides(AAm, MAA) and the zwitterionic hydrogels were lower compared to other hydrogels; the hydrogels having hydroxyl groups (HEA, HEMA), the hydrogel having HEAA monomers among the hydrogels having both hydroxyl groups and amide groups, and the hydrogels having positive charges (DMAEMA, TMA) had higher numbers of attached leukocytes; wherein the hydrogels having positive charges (DMAEMA, TMA) attached a large number of leukocytes through the electrostatic force between the hydrogels and the leukocytes. It is noted that among the hydrogels having both hydroxyl groups and amide groups, the hydrogel having HPMA monomers and the hydrogel having HEAA monomers had a significant difference in the numbers of attached leukocytes. Specifically, the number of attached leukocytes for the hydrogel having HPMA monomers was very low, while the number of attached leukocytes for the hydrogel having HEAA monomers was very high, even higher than that for the hydrogel having positive charges (DMAEMA); this indicates that hydrogel having HEAA monomers has a very high affinity for leukocytes.

In addition, the aforementioned theory of hydration layer, the experiments of plasma protein adsorption and the experiments of platelet attachment all show that hydrogel having HPMA monomers and hydrogel having HEAA monomers have excellent anti-biomolecular adhesion effect. It is noted that hydrogel having HPMA monomers did not attach leukocytes, but hydrogel having HEAA monomers attached a large number of leukocytes, hardly adsorbed plasma protein, and also hardly attached platelets. In other words, using polymers polymerized from HEAA monomers or/and HEAA monomers with other compounds allows a large number of leukocytes attach on the polymer and does not require plasma proteins and platelets to assist in the adsorption of leukocytes. It is assumed that the polymer comprising HEAA has direct affinity adsorption to the surface of leukocytes, or maybe a trace amount of intercellular adhesion molecules (ICAMs) are adsorbed on the polymer comprising HEAA to assist the affinity adsorption of leukocytes.

3. The Method of Substrate Modification 3.1 the Materials of Substrate Modification In the experiment, the surfaces of the substrates were modified to further verify the ability to capture or separate leukocytes of the present embodiment.

The test material of the examples was the aforementioned N-hydroxyethyl acrylamide (HEAA) having both a hydroxyl functional group and an amide functional group, which has the following chemical structure:

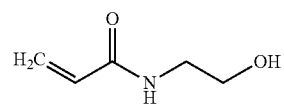

The test material of the comparative examples was positively charged N,N-dimethylaminoethyl methacrylate (DMAEMA), which has the following chemical structure:

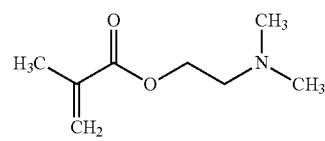

In addition, butyl methacrylate (BMA) and glycidyl methacrylate (GMA) were used for the occlusal end of the polymer to be tested, so that the polymer to be tested can physically adsorb to the surface of the substrate. BMA and GMA respectively have the following chemical structures:

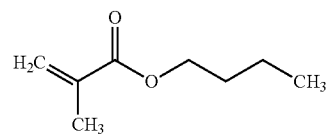

BMA

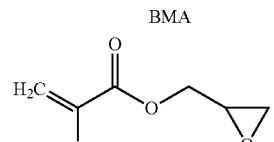

GMA 4,4'-Azobis(4-cyanovaleric acid) (ACVA) was used as an initiator, and it has the following chemical structure:

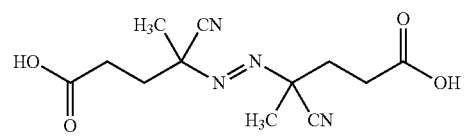 [SMILES: CC(C#N)(CCC(=O)O)/N=N/C(C)(C#N)CCC(=O)O]

The material of the substrate was polypropylene (PP) and polyethylene terephthalate (PET). PP and PET respectively have the following chemical structures:

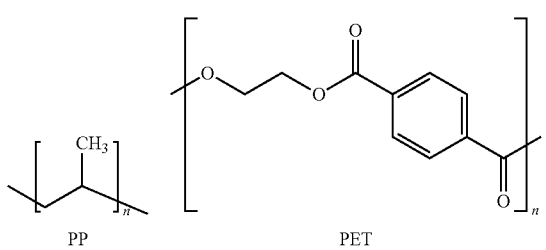

3.2 Preparation of Polymers for Substrate Modification

BMA and GMA were used as the occlusion end of the substrate, HEAA and DMAEMA were used as the functional end, and they are mixed according to the ratio (the occlusion end accounts for 70%, and the functional end accounts for 30%), then the initiator ACVA was added, and the solvent was ethanol. Next, polymerization was carried out for 24 hours in an environment at 70° C. to prepare BMA-r-HEAA polymer, BMA-r-DMAEMA polymer, BMA-r-GMA-r-HEAA polymer, and BMA-r-GMA-r-DMAEMA polymer. After the reaction was completed, the products were precipitated by using deionized water as a precipitating agent and then dried.

3.3 Surface Modification of the Substrates

PP and PET were selected as the substrates to be modified.

3.3.1 PP Substrate Modification by Physical Adsorption

BMA-r-HEAA polymer, BMA-r-DMAEMA polymer, BMA-r-GMA-r-HEAA polymer, and BMA-r-GMA-r-DMAEMA polymer were taken respectively, ethanol was used as the solvent, and the respective polymer solutions were prepared. PP substrates were respectively taken and cut to a suitable size, soaked in the polymer solutions for 1 minute, then the residual solution on the surfaces was washed away with deionized water, and then the PP substrates were dried. Accordingly, surface-modified PP substrates respectively coated with BMA-r-HEAA polymer, BMA-r-DMAEMA polymer, BMA-r-GMA-r-HEAA polymer, and BMA-r-GMA-r-DMAEMA polymer can be obtained.

3.3.2 PET Substrate Modification by UV Treatment

HEAA and DMAEMA monomers were taken, ethanol was used as a solvent, and the monomer solutions were prepared, respectively. PET substrates were taken and cut to a suitable size, soaked in the monomer solutions, placed under 7200 W of UV light for 2 minutes, then the residual solution on the surfaces was washed away with deionized water, and then the PET substrates were dried. Accordingly, surface-modified PET substrates respectively grafted with HEAA monomers and DMAEMA monomers can be obtained.

3.4 Identification of Nuclear Magnetic Resonance (NMR)

10 mg of each of the above-mentioned polymers was weighed and dissolved in 1 mL of methanol (d-MeOH), and a solution of 10 mg/mL was placed in an NMR tube and delivered to the Instrumentation Center of National Central University in Taiwan for performing measurements. Then the chemical structures and the ratios of the monomers of the polymers were analyzed and calculated by the characteristic peaks of the spectra.

3.5 Density Measurement of Surface Modification

Before the modification, the PP substrates and the PET substrates were weighted by a microbalance. After the surfaces were modified completely, the substrates were dried, and the weights of the surfaces were weighed via a microbalance. The weight of the polymer modified on the surface of the substrate can be obtained by calculating the difference in weights of the substrate before and after the experiment. Finally, the weight of the polymer per unit area, i.e., the coverage density, can be obtained by conversion.

3.6 Measurement of X-Ray Photoelectron Spectroscopy (XPS) Analyzer

The surface element component analysis of PP and PET surfaces modified by HEAA was carried out by using X-ray photoelectron spectroscopy Analyzer (XPS). Then the nitrogen contents of the various modified surfaces were compared by the characteristic peaks of the spectra.

3.7 Attachment Test of Blood Cell

First, the substrates were soaked in PBS buffer for half an hour. Next, after the liquid was blotted dry, 1 ml of erythrocyte concentrate, leukocyte concentrate, and platelet concentrate were respectively used to cover the surfaces of the substrates, and then the substrates were placed in an oven at 37° C. for 2 hours of attachment. Then, the unattached blood cells on the surfaces of the substrates were washed away with PBS buffer, the substrates were soaked in glutaraldehyde for one day to fix the cells, and the attachments of the blood cells were observed on surfaces of polypropylene disks by a conjugated laser scanning electron microscope (LSCM).

3.8 Blood Filtration Test

The modified substrates were cut into a circle having a diameter of 2.6 cm, 5 layers of the substrates were stacked, and then the substrates were placed and locked tightly in an acrylic filter (similar to the exemplary example shown in FIG. 2). 5 ml of platelet concentrate was taken for performing filtration. Next, the blood products before and after the filtration were examined using a blood cell counter to calculate the leukocyte removal rate and the platelet retention rate.

4. The Detection Results of Substrate Modification

4.1 Analysis Results of Nuclear Magnetic Resonance (NMR)

Figure 8:
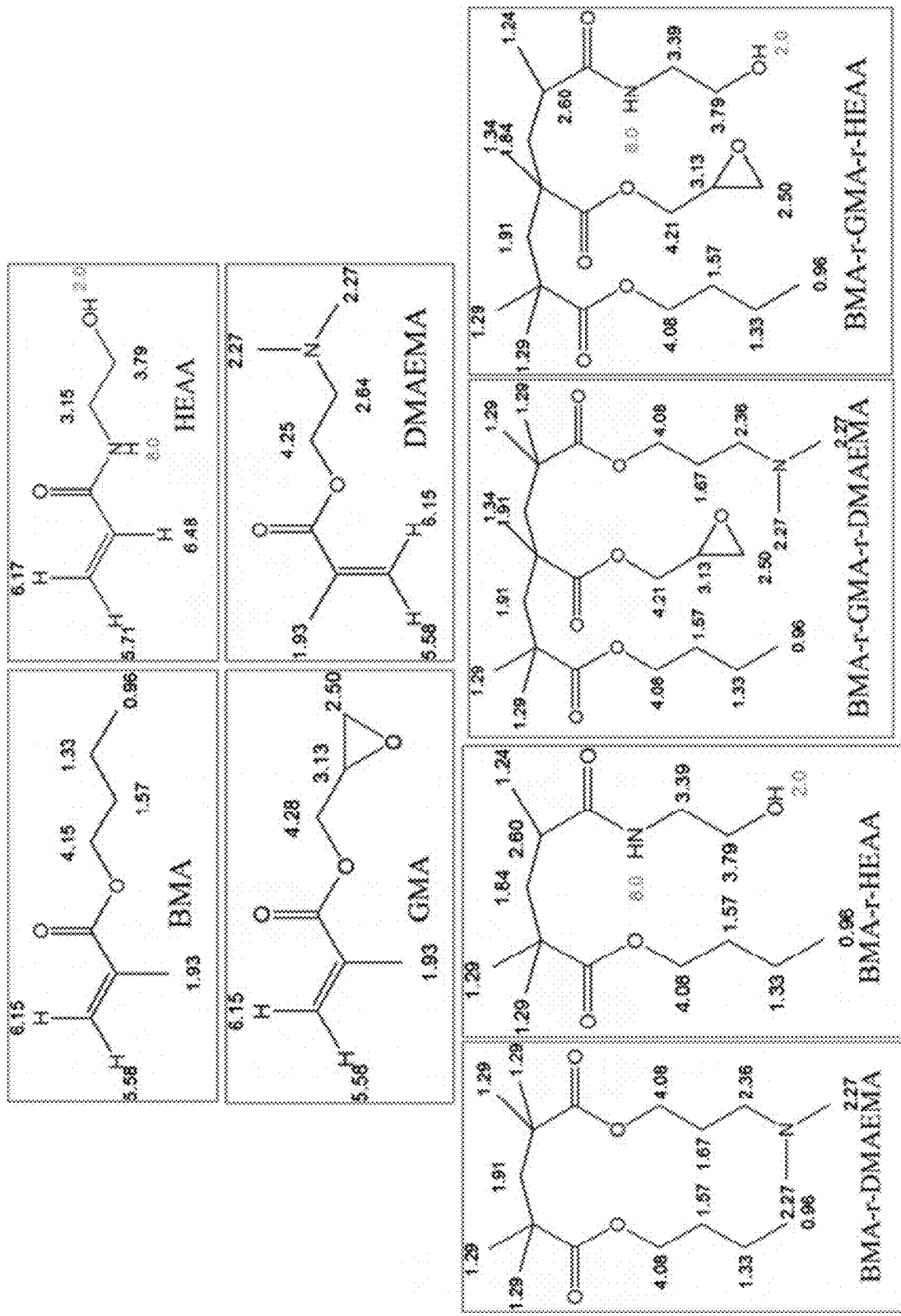
FIG. 8 shows the structural formulas and the chemical shifts of the signals in NMR spectra of the various monomer compounds and polymer compounds in accordance with some embodiments of the present invention.
Figure 9:
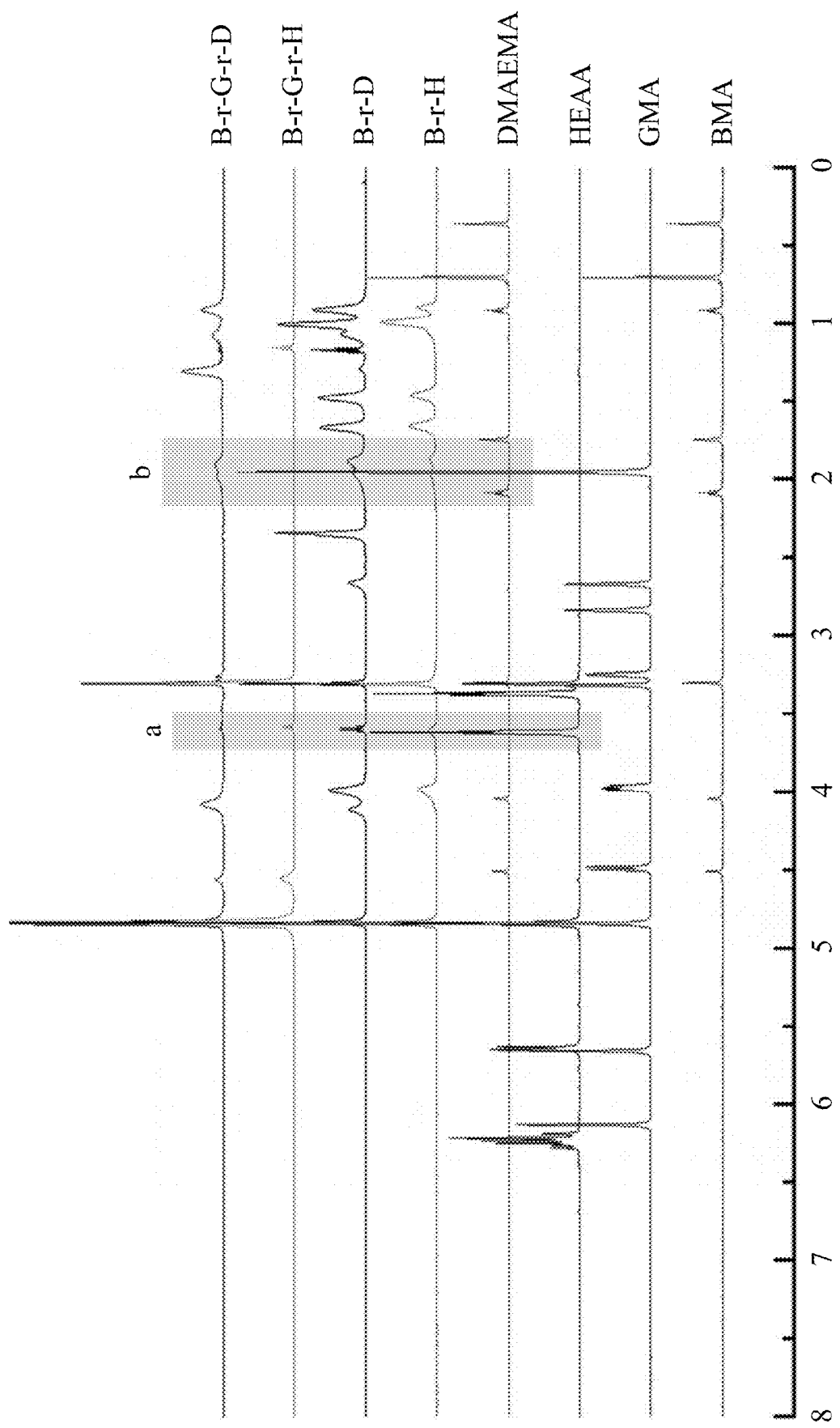
FIG. 9 shows the chemical structural spectra of nuclear magnetic resonance spectroscopy (NMR) of the various monomer compounds and polymer compounds in accordance with some embodiments of the present invention.

FIG. 8 shows the structural formula and the chemical shift of the various monomer compounds and polymer compounds. In addition, as shown in Table 1 below, for the convenience in the following description, the polymer compounds such as BMA-r-HEAA, BMA-r-DMAEMA, BMA-r-GMA-r-HEAA, and BMA-r-GMA-r-DMAEMA are respectively abbreviated as B-r-H, B-r-D, B-r-G-r-H, and B-r-G-r-D. FIG. 9 shows the NMR spectra of various monomer and polymer structures. According to the analysis of NMR, the characteristic peak of HEAA mainly appeared at "a" site, the characteristic peak of DMAEMA mainly appeared at "b" site. It can be seen that the polymer compounds used in this experiment have been successfully synthesized according to the NMR spectra.

TABLE 1

| Names of polymer | Abbreviation |
|---|---|
| BMA-r-HEAA | B-r-H |
| BMA-r-DMAEMA | B-r-D |
| BMA-r-GMA-r-HEAA | B-r-G-r-H |
| BMA-r-GMA-r-DMAEMA | B-r-G-r-D |

4.2 Coverage Density Measurement Results of PP and PET Substrate

Figure 10:
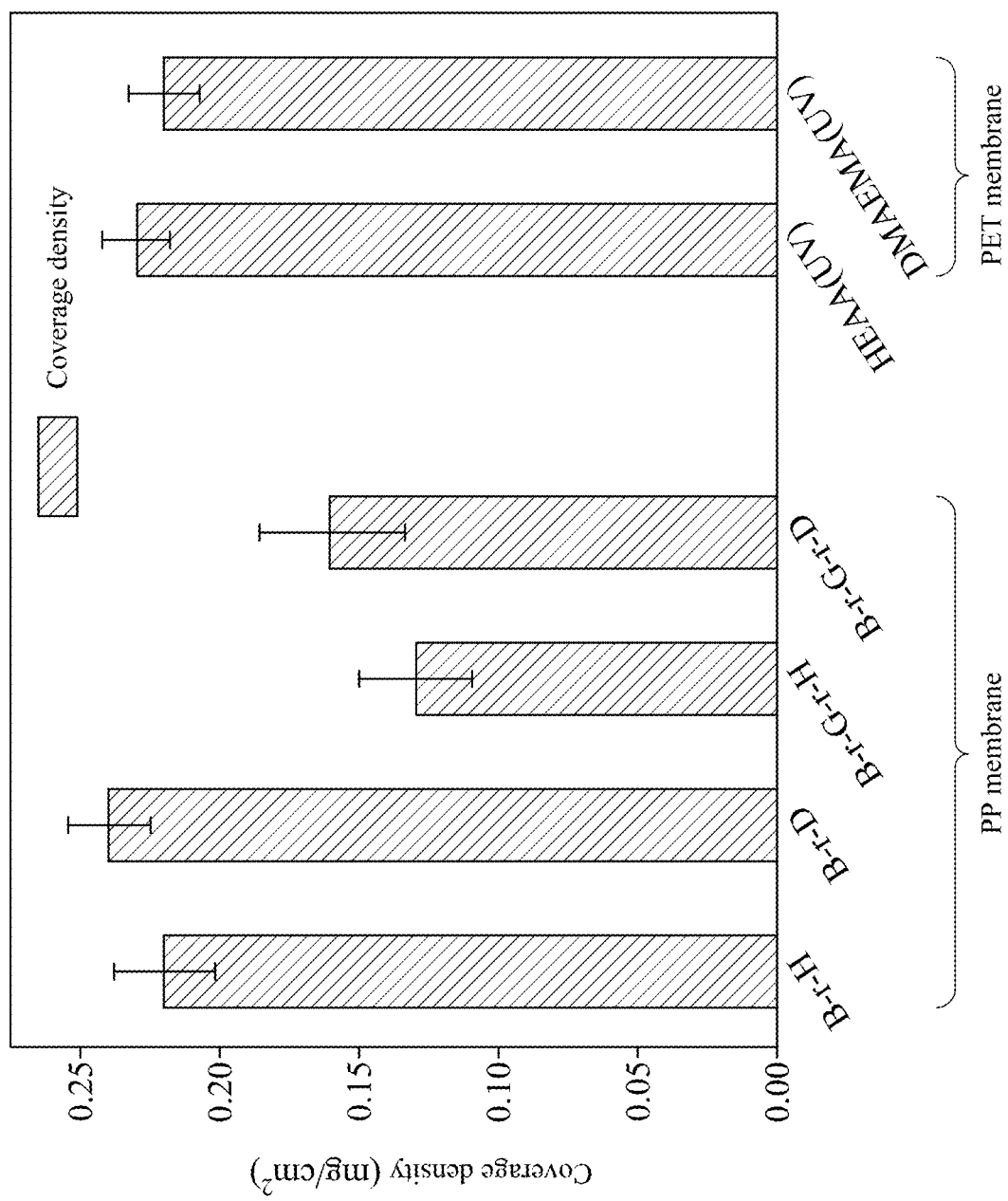
FIG. 10 shows the coverage densities of the graft materials on the polypropylene (PP) substrates and the polyethylene terephthalate (PET) substrates in accordance with some embodiments of the present invention.

FIG. 10 shows the results of the coverage densities of the various polymer compounds. The PP membranes are PP substrates respectively coated with polymer compounds B-r-H, B-r-D, B-r-G-r-H, and B-r-G-r-D. The PET membranes are PET substrates respectively grafted with HEAA and DMAEMA. By weighting the weights of the substrates before and after modification and measuring the surface areas of the substrates, the various polymer coating densities for the surfaces of the substrates can be calculated, and the densities were between 0.1 to 0.25 mg/cm$^2$.

4.3 Measurement Results of X-Ray Photoelectron Spectroscopy (XPS) Analyzer

Figure 11:
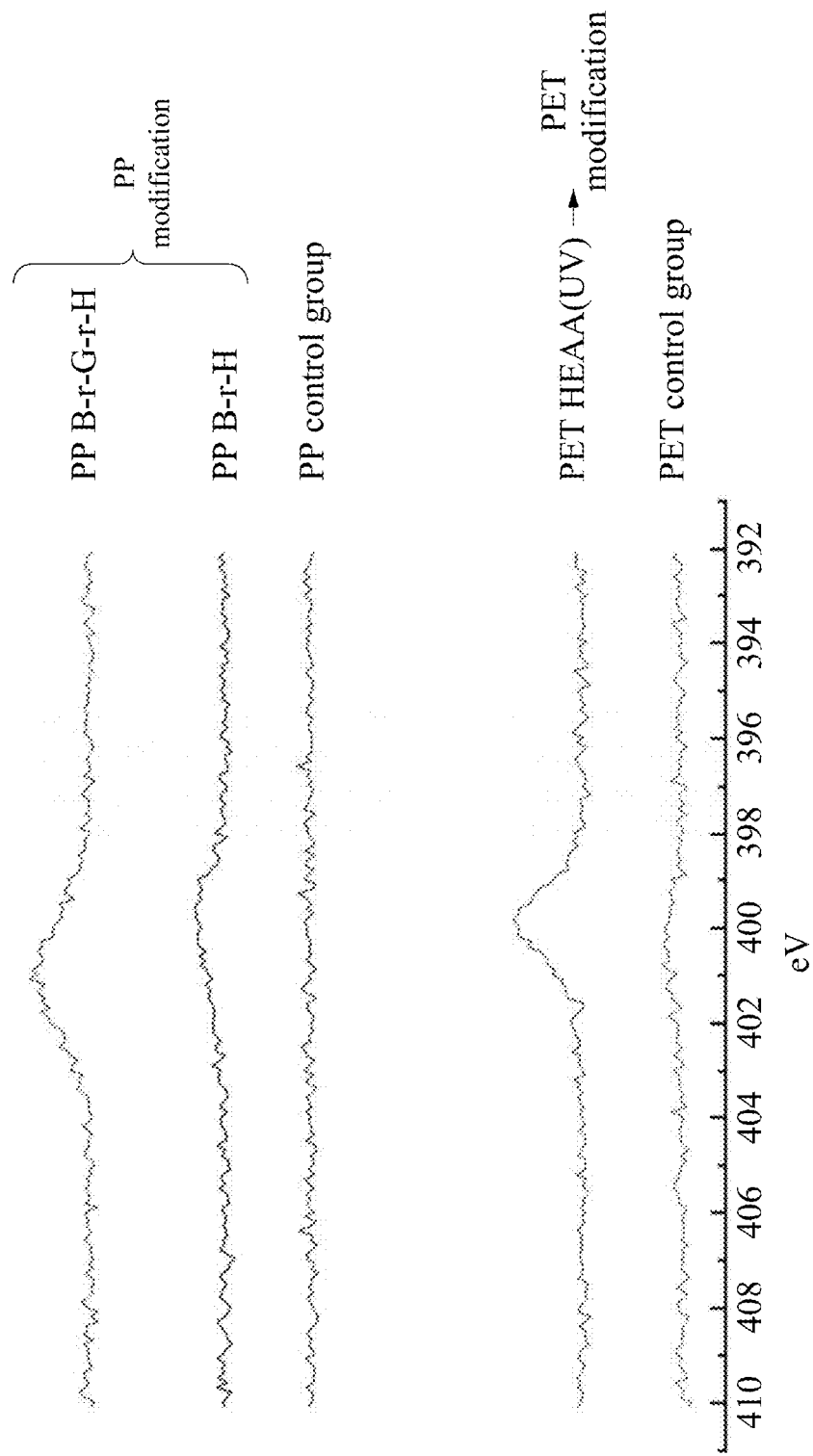
FIG. 11 shows the analysis spectra of photoelectron spectrometer for the nitrogen elements on the surfaces of the PP substrates and the PET substrates in accordance with some embodiments of the present invention.

The surfaces of the modified substrates can be analyzed by surface X-ray photoelectron spectroscopy; the difference before and after the modification can be seen from the analysis of the nitrogen elements. FIG. 11 shows the analysis spectra of the nitrogen elements on the upper surfaces of the substrates. The PP control group and the PET control group were unmodified PP substrate and unmodified PET substrate, respectively. The ratios of the surface elements before and after HEAA modification are summarized in detail in Table 2 below. Referring to FIG. 11 and Table 2 below, it is known that no nitrogen signal generated on the unmodified PP substrate. On the contrary, the ratios of nitrogen on the surfaces of PET and PP substrates modified by HEAA monomers or polymers containing HEAA increased significantly, and the characteristic peaks of nitrogen appeared at 399~402 eV.

TABLE 2

| Element content (%) | | C1s | O1s | N1s |
|---|---|---|---|---|
| Modified PET membrane | Control group | 71.76 | 27.07 | 1.17 |
| | HEAA (UV) | 70.24 | 26.76 | 3 |
| Modified PP membrane | Control group | 98.2 | 1.8 | 0 |
| | B-r-H | 79.84 | 18.1 | 2.05 |
| | B-r-G-r-H | 76.22 | 21.04 | 2.75 |

4.4 Attachment Test Results of Blood Cell

FIGS. 12 to 15 show the blood cell attachment images and the cell counts of the surfaces of the PP substrates and the PET substrates before and after modification.

Figure 12:
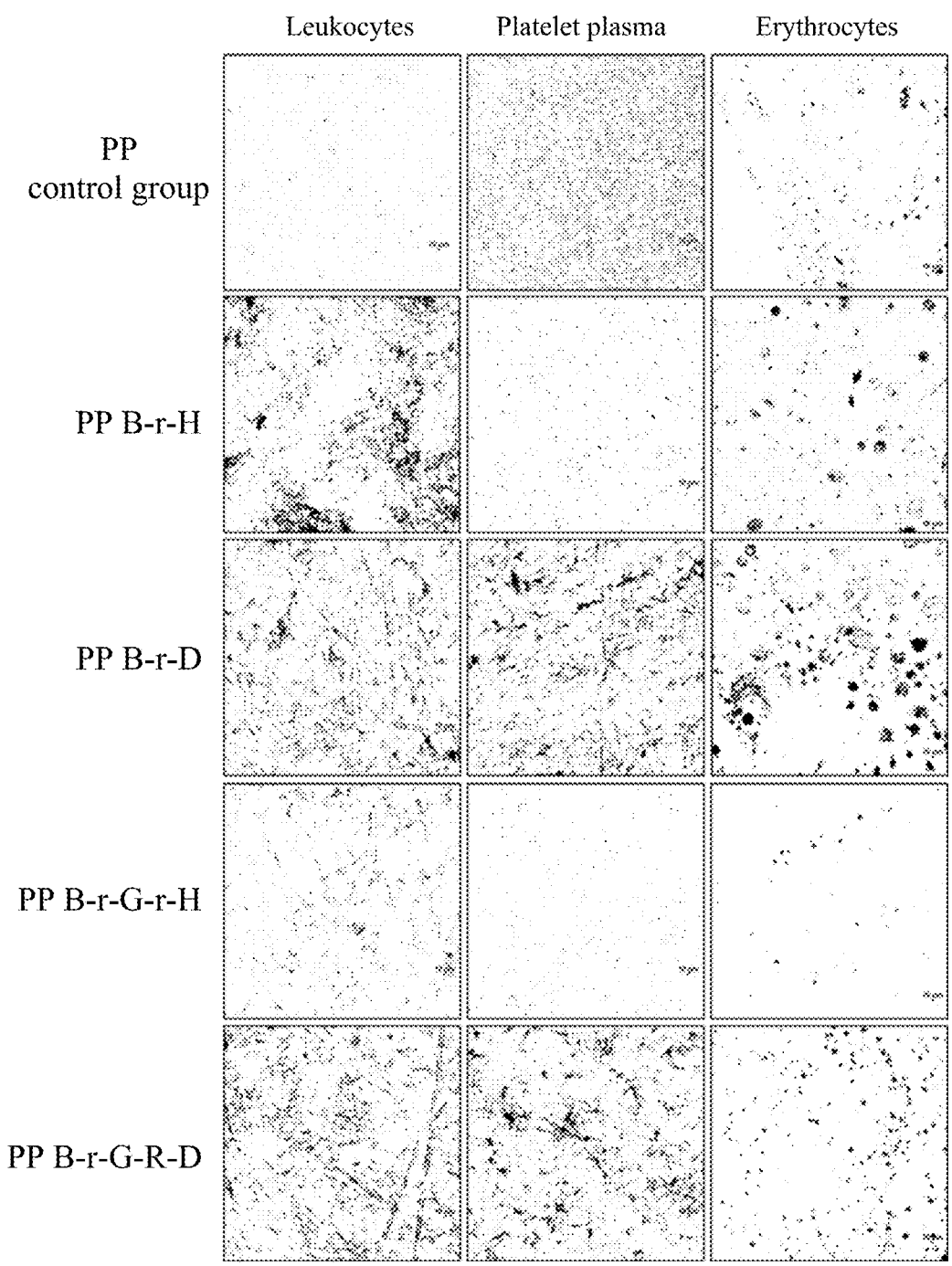
FIG. 12 shows the qualitative results for images of the attachments of leukocytes, platelets, and erythrocytes on the various PP substrates in accordance with some embodiments of the present invention.
Figure 13:
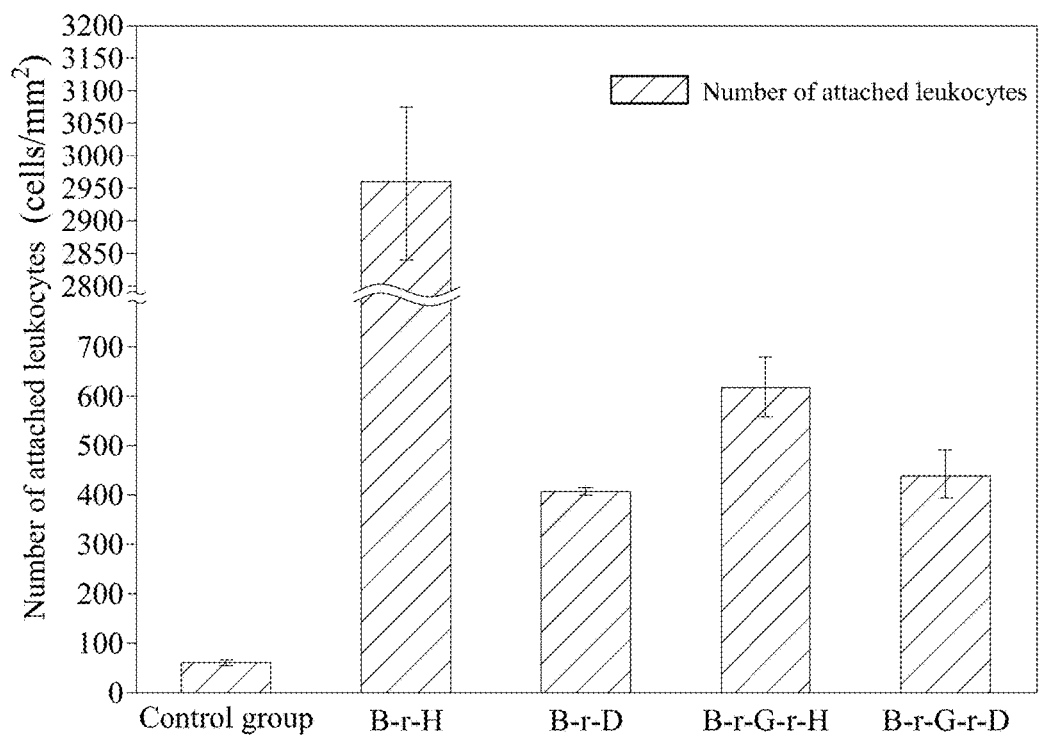
FIG. 13 shows the quantitative results from images of the attachments of leukocytes, platelets, and erythrocytes on the various PP substrates in accordance with some embodiments of the present invention.
Figure 13:
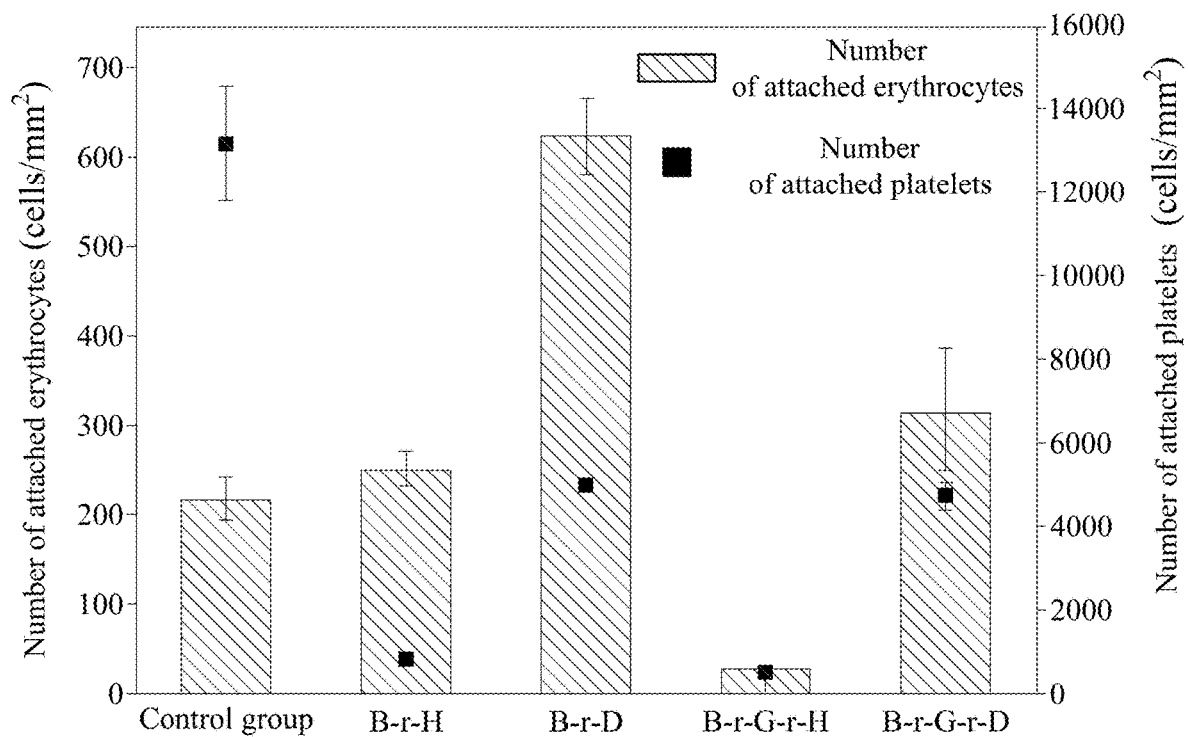

First, referring to FIGS. 12 and 13, which show the result of blood cell attachment after physical coating modification. In FIG. 12, it is apparent that the images of platelet plasma and erythrocytes on the PP substrates containing HEAA (PP B-r-H and PP B-r-G-r-H) are lighter, this means that the surfaces of the substrates were less likely to attach platelet plasma and erythrocytes. In addition, the image of leukocytes on the PP substrate containing B-r-H was significantly darker; this means that the surface of the substrate was easier to attach leukocytes. In FIG. 13, the upper graph shows the results of the numbers of attached leukocytes, and the lower graph shows the results of the numbers of attached erythrocytes. Accordingly, for PP substrates containing HEAA, the surfaces of the PP substrates have HEAA which can effectively capture leukocytes, and the surfaces had fewer numbers of attached platelets and erythrocytes. The surfaces of PP substrates (PP B-r-D and PP B-r-G-r-D) containing DMAEMA not only captured leukocytes but also had relatively higher numbers of attached platelets and erythrocytes.

Figure 14:
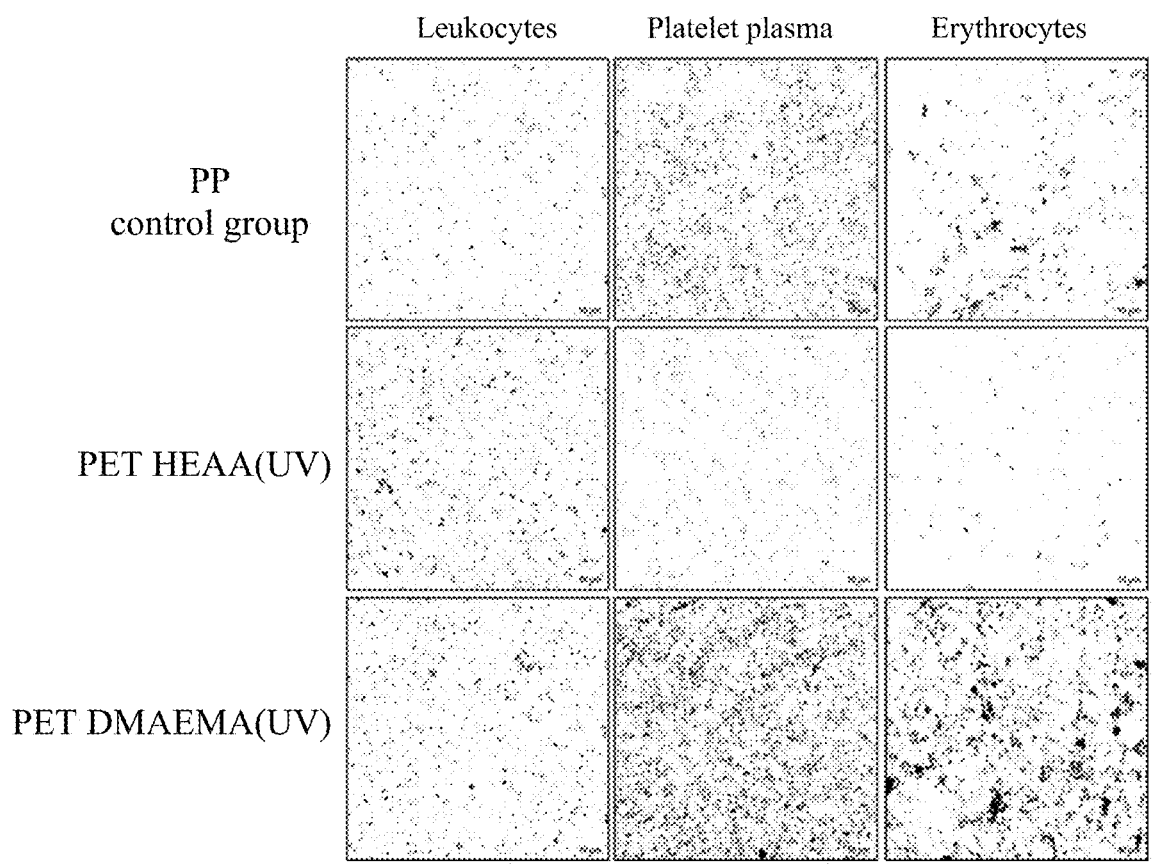
FIG. 14 shows qualitative results for images of the attachments of leukocytes, platelets, and erythrocytes on the various PET substrates in accordance with some embodiments of the present invention.
Figure 15:
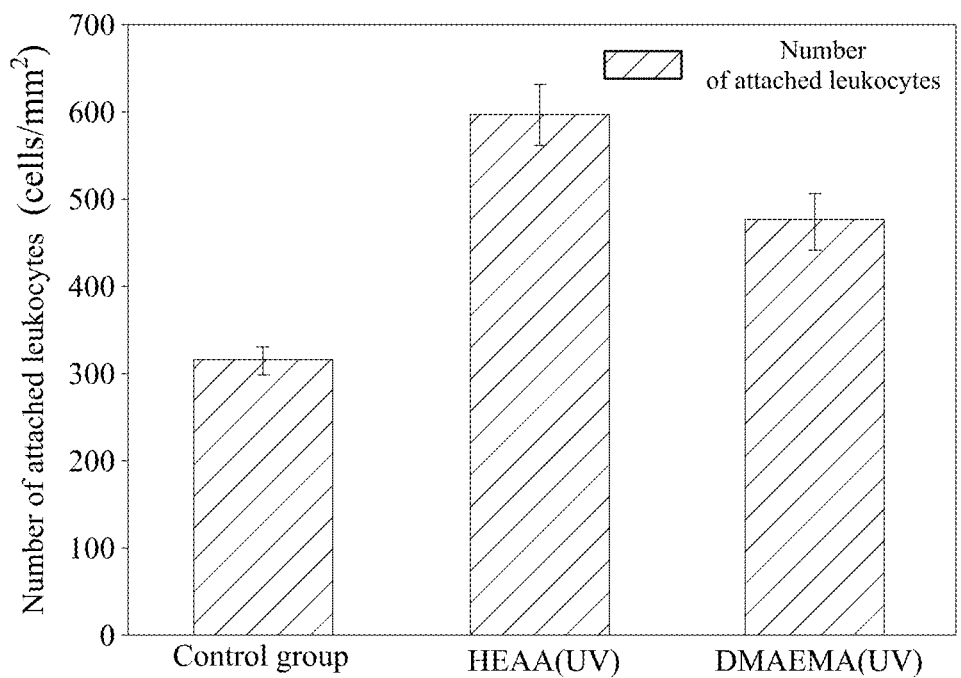
FIG. 15 shows quantitative results from images of the attachments of leukocytes, platelets, and erythrocytes on the various PET substrates in accordance with some embodiments of the present invention.
Figure 15:
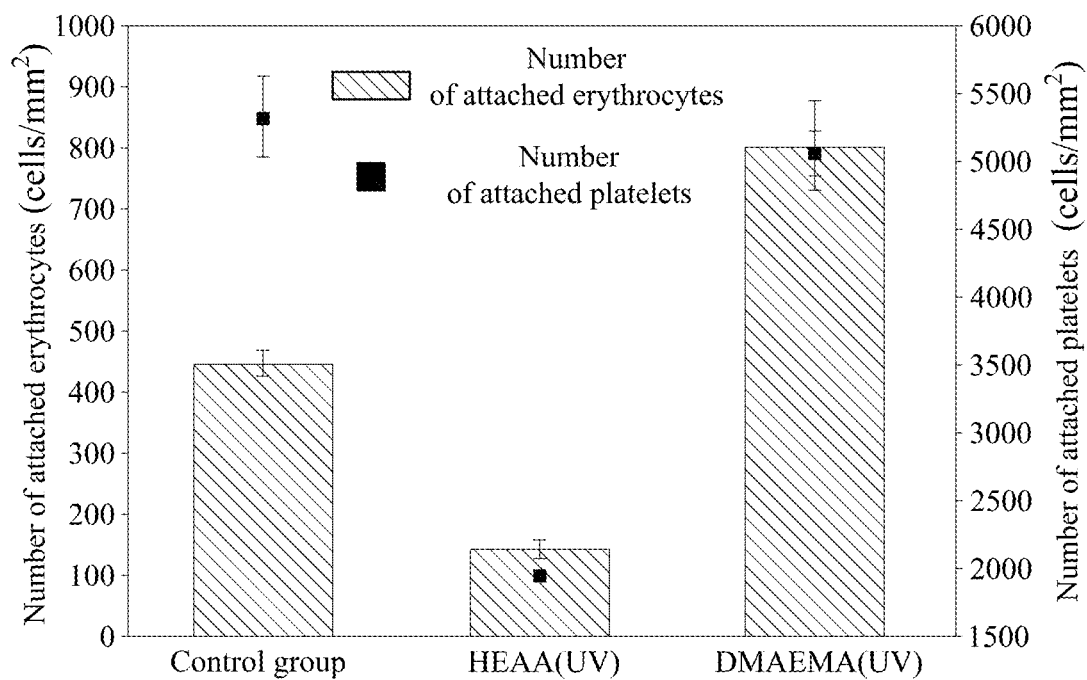

Please continue to refer FIGS. 14 and 15, which show the results of blood cell attachment for PET substrate modified by chemical grafting. In FIG. 14, it is apparent that the images of platelet plasma and erythrocytes on the PET substrate grafted with HEAA were much lighter; this means that the substrate was less likely to attach platelet plasma and erythrocytes. In addition, the image of the leukocytes on the PET substrate grafted with HEAA was significantly darker; this means that the surface of the substrate was easier to attach leukocytes. In FIG. 14, the upper graph shows the results of the numbers of the attached leukocytes, and the lower graph shows the results of the numbers of the attached erythrocytes. Thus, after UV treatment, the surface of the PET substrate grafted with HEAA has the ability to capture leukocytes and simultaneously decrease the numbers of attached of platelets and erythrocytes. Conversely, all three blood cell types attached to the surfaces of the PET substrates grafted with DMAEMA.

In addition, in the attachment test of blood cells, the erythrocyte concentrate actually contained trace leukocytes, and in the aforementioned attachment images of FIGS. 12 and 14, the substrate containing HEAA can still capture the trace leukocytes in the erythrocyte concentrate. It is shown that the surface of the substrate modified with HEAA has specificity for capturing leukocytes.

4.5 Results of Blood Filtration Test

Similar to the aforementioned blood filtration test, the modified substrates were used to filter the platelet concentrate. The various blood cell types in blood product before and after filtration can be acquired from measurement by a blood cell counter, and the leukocyte removal rate and the platelet retention rate were calculated.

As shown in Table 3 below, WBC is white blood cell, and PLT is platelet. According to Table 3, the substrates modified by HEAA had a leukocyte capture rate of at least 87% and can retain more than 86% of platelets. That is, when platelet concentrate (a platelet concentrate containing leukocytes) flow through the modified substrate, most of the leukocytes attach to the substrate and the remaining filtrate retain most of the platelets. Accordingly, the examples of the present invention have very high specificity for capturing leukocytes (and does not cause capture or attachment of erythrocytes and platelets) and is an excellent material for depleting leukocytes in platelet concentrate. Of course, in other embodiments, it is possible to directly prepare platelet concentrate by passing a whole blood sample through the aforementioned substrates, followed by erythrocyte depletion techniques.

Compared with the conventional methods in which B-r-D, B-r-G-r-D, and DMAEMA were used to capture, separate, or filter leukocytes, the capturing ability for leukocytes of the present embodiments is enhanced while the platelet retention rate is maintained; therefore, it is apparent that the effects of B-r-H, B-r-G-r-H, HEAA are achieved by mechanisms different from the mechanisms of previous methods.

TABLE 3

| | | Before filtration | | After filtration | | Performance of filtration | |
|---|---|---|---|---|---|---|---|
| | | WBC ($10^3$/μl) | PLT ($10^3$/μl) | WBC ($10^3$/μl) | PLT ($10^3$/μl) | Removal rate of WBC (%) | Retention rate of PLT (%) |
| Modified PP membrane | Control group | — | — | — | — | — | — |
| | B-r-H | 0.39 | 1224 | 0.03 | 1112 | 92.31% | 90.85% |
| | B-r-G-r-H | 0.39 | 1224 | 0.05 | 1059 | 87.18% | 86.52% |

TABLE 3-continued

|  |  | Before filtration | | After filtration | | Performance of filtration | |
|---|---|---|---|---|---|---|---|
|  |  | WBC ($10^3/\mu l$) | PLT ($10^3/\mu l$) | WBC ($10^3/\mu l$) | PLT ($10^3/\mu l$) | Removal rate of WBC (%) | Retention rate of PLT (%) |
| Modified PET membrane | B-r-D | 0.39 | 1209 | 0.26 | 684 | 35.00% | 56.58% |
|  | B-r-G-r-D | 0.4 | 1209 | 0.24 | 751 | 40.00% | 62.12% |
|  | Control group | 0.4 | 1209 | 0.37 | 659 | 7.50% | 54.51% |
|  | HEAA (UV) | 0.39 | 1224 | 0.05 | 1077 | 87.18% | 87.99% |
|  | DMAEMA (UV) | 0.4 | 1209 | 0.12 | 598 | 70.00% | 49.46% |

The foregoing outlines features of several examples so that those of ordinary skill in the art may better understand the aspects of the present disclosure. Those of ordinary skill in the art should appreciate that they may readily use the present disclosure as a basis for designing or modifying other processes and structures for carrying out the same purposes and/or achieving the same advantages of the examples introduced herein. Those of ordinary skill in the art should also realize that such equivalent constructions do not depart from the spirit and scope of the present disclosure, and that they may make various changes, substitutions, and alterations herein without departing from the spirit and scope of the present disclosure.

What is claimed is:

1. A method comprising:
providing a device for blood treatment, wherein the device comprises a polymer consisting essentially of an amide-hydroxyl-containing monomer and an other monomer, wherein the other monomer is an anchoring unit or a crosslinking agent, the polymer is prepared from polymerizing the amide-hydroxyl-containing monomer with the other monomer, wherein the amide-hydroxyl-containing monomer has a structure of formula (1):

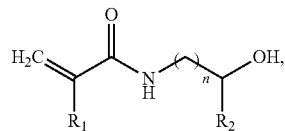

(1)

in formula (1), $R_1$ is independently selected from the group consisting of hydrogen, methyl group, ethyl group, hydroxyl group, one of from C1 to C12 carbon chain, and benzene ring, $R_2$ is independently selected from the group consisting of hydrogen, methyl group, ethyl group, one of from C1 to C6 carbon chain, amine group, and benzene ring, and n is an integer of 1 to 5, wherein a repeat unit of the polymer has an amide group and a hydroxyl group from the amide-hydroxyl-containing monomer;
providing a blood sample, wherein the blood sample comprises leukocytes; and
passing the blood sample through the device, wherein the repeat unit of the polymer specifically adsorb the leukocytes.

2. The method of claim 1, wherein the anchoring unit is butyl methacrylate (BMA) or glycidyl methacrylate (GMA).

3. The method of claim 1, wherein the crosslinking agent is N, N'-methylenebisacrylamide (NMBA), ethylene glycol dimethacrylate (EGDMA), PLA-PEG-PLGA copolymer (PLA: Polylactic Acid, PEG: Polyethylene glycol, PLGA: Poly (lactic acid-co-glycolic acid)), or poly(ethylene glycol) diacrylate (PEGDA).

4. A device for capturing or separating leukocytes, comprising:
a housing; and
a body in the housing,
wherein the body comprises a substrate and a polymer disposed on the substrate, the polymer is consisting essentially of an amide-hydroxyl-containing monomer and an other monomer, the other monomer is an anchoring unit or a crosslinking agent,
wherein the polymer is prepared by a polymerized reaction using the amide-hydroxyl-containing monomer and the other monomer, the amide-hydroxyl-containing monomer has a structure of formula (1):

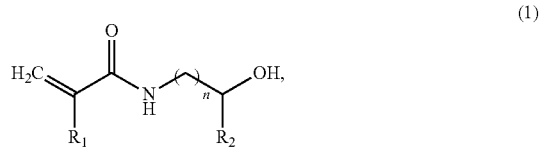

(1)

in formula (1), $R_1$ is independently selected from the group consisting of hydrogen, methyl group, ethyl group, hydroxyl group, one of from C1 to C12 carbon chain, and benzene ring, $R_2$ is independently selected from the group consisting of hydrogen, methyl group, ethyl group, one of from C1 to C6 carbon chain, amine group, and benzene ring, and n is an integer of 1 to 5, wherein a repeat unit from the formula (1) of the polymer has an —NH— group and an —OH group, and the repeat unit is configured to specifically adsorb leukocytes.

5. The device for capturing or separating leukocytes of claim 4, wherein the amide-hydroxyl-containing monomer is N-hydroxyethyl acrylamide.

6. The device for capturing or separating leukocytes of claim 4, wherein the polymer is a copolymer, and the polymer is copolymerized from the amide-hydroxyl-containing monomer with the anchoring unit.

7. The device for capturing or separating leukocytes of claim 6, wherein the anchoring unit is butyl methacrylate (BMA) or glycidyl methacrylate (GMA).

8. The device for capturing or separating leukocytes of claim 4, wherein the polymer is a segmented polymer.

9. The device for capturing or separating leukocytes of claim 4, wherein the polymer is a crosslinked copolymer.

10. The device for capturing or separating leukocytes of claim 9, wherein the crosslinking agent has a diacrylate functional group.

11. The device for capturing or separating leukocytes of claim 10, wherein the crosslinking agent is N, N'-methylenebisacrylamide (NMBA), ethylene glycol dimethacrylate (EGDMA), PLA-PEG-PLGA copolymer (PLA: Polylactic Acid, PEG: Polyethylene glycol, PLGA: Poly (lactic acid-co-glycolic acid)), or poly(ethylene glycol) diacrylate (PEGDA).

* * * * *